(12) United States Patent
Kim et al.

(10) Patent No.: US 12,102,371 B2
(45) Date of Patent: Oct. 1, 2024

(54) FILTER MODULE USED FOR COOLING SYSTEM AND COOLING DEVICE

(71) Applicants: RECENSMEDICAL, INC., Ulsan (KR); UNIST (ULSAN NATIONAL INSTITUTE OF SCIENCE AND TECHNOLOGY), Ulsan (KR)

(72) Inventors: Gun-Ho Kim, Ulsan (KR); Boo Seong Park, Hwaseong-si (KR); Chulho Lee, Yongin-si (KR)

(73) Assignees: RecensMedical, Inc., Ulsan (KR); UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 0 days.

(21) Appl. No.: 18/521,961

(22) Filed: Nov. 28, 2023

(65) Prior Publication Data

US 2024/0090934 A1    Mar. 21, 2024

Related U.S. Application Data

(63) Continuation of application No. PCT/KR2022/007611, filed on May 27, 2022.

(30) Foreign Application Priority Data

May 31, 2021  (KR) .......................... 10-2021-0070379

(51) Int. Cl.
*A61B 18/02* (2006.01)
*A61F 7/00* (2006.01)
(Continued)

(52) U.S. Cl.
CPC ........ *A61B 18/0218* (2013.01); *A61F 7/0085* (2013.01); *B01D 35/02* (2013.01);
(Continued)

(58) Field of Classification Search
CPC ...... A61B 18/0218; A61B 2018/00029; B05B 15/40; A61F 7/0085; B01D 35/02;
(Continued)

(56) References Cited

U.S. PATENT DOCUMENTS 3,743,188 A * 7/1973 Wagner .................... B05B 9/01
239/526
7,188,787 B2 * 3/2007 Cannon ................... C02F 1/003
239/575
(Continued)

FOREIGN PATENT DOCUMENTS

CN       101035735 A     9/2007
CN       101267869 A     9/2008
(Continued)

OTHER PUBLICATIONS

International Search Report and Written Opinion mailed Sep. 1, 2022 in International Application No. PCT/KR2022/007611.
(Continued)

*Primary Examiner* — Steven J Ganey
(74) *Attorney, Agent, or Firm* — Knobbe, Martens, Olson & Bear, LLP

(57) ABSTRACT

Proposed is a filter module including a filter that filters impurities out in the coolant emitted from a cartridge which includes a housing and a cap. The filter module may include not only a filter accommodation member including a support surface and a perforating member protruding from the support surface but also a first sealing member with a first external diameter including a through-hole fitted into the perforating member. The first sealing member may be transformed into a shape with a second external diameter—the second external diameter is smaller than the first external diameter—corresponding to the width of an inlet of the
(Continued)

housing in which the first sealing member accommodates a cap when the cap is perforated by the perforating member.

13 Claims, 19 Drawing Sheets

(51) Int. Cl.
  *B01D 35/02* (2006.01)
  *B01D 35/30* (2006.01)
  *B05B 15/40* (2018.01)
  *A61B 18/00* (2006.01)
  *A61N 5/06* (2006.01)

(52) U.S. Cl.
  CPC .............. *B01D 35/30* (2013.01); *B05B 15/40* (2018.02); *A61B 2018/00029* (2013.01); *A61N 5/0616* (2013.01); *B01D 2201/34* (2013.01); *B01D 2221/10* (2013.01)

(58) Field of Classification Search
  CPC .......................... B01D 35/30; B01D 2201/34; B01D 2221/10; A61N 5/0616
  USPC ..... 239/525, 526, 302, 309, 575, 590–590.5
  See application file for complete search history.

(56) References Cited

U.S. PATENT DOCUMENTS

| | | |
|---|---|---|
| 7,484,643 B2 | 2/2009 | Amaral et al. |
| 10,188,972 B2 | 1/2019 | You et al. |
| 11,547,971 B2 | 1/2023 | Lee |
| 2007/0199876 A1 | 8/2007 | Tubby et al. |
| 2013/0184694 A1 | 7/2013 | Fourkas et al. |
| 2016/0096187 A1 | 4/2016 | Kakumu |
| 2021/0290430 A1 | 9/2021 | Kim |

FOREIGN PATENT DOCUMENTS

| | | |
|---|---|---|
| CN | 107215905 A | 9/2017 |
| CN | 109648372 A | 4/2019 |
| JP | 2002-052436 A | 2/2002 |
| JP | 2017-030110 A | 2/2017 |
| JP | 2017-148799 A | 8/2017 |
| KR | 20-0419179 Y1 | 6/2006 |
| KR | 10-1935597 B1 | 1/2019 |
| KR | 10-2020-0097300 A | 8/2020 |
| WO | WO 2019/143165 A1 | 7/2019 |
| WO | WO 2020/117030 A1 | 6/2020 |

OTHER PUBLICATIONS

Notice of Allowance dated Sep. 18, 2023 in Korean Application No. 10-2023-7029742 (which claims priority to KR 10-2021-0070379 filed on May 31, 2021).

Chinese First Office Action, with English translation, dated May 18, 2024, for CN 202280039261.7.

European Extended Search Report dated Jun. 13, 2024 for EP 22816406.7.

\* cited by examiner

| elapsed time | cartridge weight g(consumption amount g) | | |
|---|---|---|---|
| | comparative example | experimental example | |
| | cartridge A | cartridge A | cartridge b |
| initial time | 74 | 74 | 45 |
| 24h (1d) | X | 73 (-1.0) | 44.8 (-2.2) |
| 48h (2d) | | 72.6 (-0.4) | 42.8 (-2.0) |
| 72h (3d) | | 72.4 (-0.2) | 36.6 (-6.2) |
| 96h (4d) | | 72.3 (-0.1) | 33.8 (-2.8) |

FIG. 10 experimental example comparative example

| | cartridge weight g(consumption amount g) | | | | | |
|---|---|---|---|---|---|---|
| | initial time | 8h (0.5d) | 24h (1d) | 48h (2d) | 72h (3d) | |
| comparative example | 74 | 0 (-74) | | | | |
| experimental example | 70 | 70 (0) | 70 (0) | 70 (0) | 70 (0) | |
| | 70 | 70 (0) | 70 (0) | 70 (0) | 70 (0) | |
| | 70 | 70 (0) | 70 (0) | 70 (0) | 70 (0) | |
| | 70 | 70 (0) | 70 (0) | 70 (0) | 70 (0) | |
| | 70 | 70 (0) | 70 (0) | 70 (0) | 70 (0) | |
| | 70 | 70 (0) | 70 (0) | 70 (0) | 70 (0) | |
| | 70 | 70 (0) | 70 (0) | 70 (0) | 68.7 (-0.3) | |
| | 70 | 70 (0) | 70 (0) | 70 (0) | 70 (0) | |
| | 70 | 70 (0) | 70 (0) | 70 (0) | | |
| | 70 | 70 (0) | 70 (0) | 70 (0) | | |

FIG. 16

FILTER MODULE USED FOR COOLING SYSTEM AND COOLING DEVICE

CROSS-REFERENCE TO RELATED APPLICATIONS

This application is a continuation application, and claims the benefit under 35 U.S.C. § 120 and § 365 of PCT Application No. PCT/KR2022/007611 filed on May 27, 2022 which claims priority to Korean Patent Application No. 10-2021-0070379 filed on May 31, 2021, both of which are hereby incorporated by reference in their entirety.

BACKGROUND

Technical Field

The present disclosure relates to a filter module for use in a cooling system and a cooling device that perform cooling.

Description of Related Technology

In modern society, interest in skin treatment or skin care is rapidly increasing in a social environment where skin disease is increasing and interest in beauty culture is rapidly increasing.

SUMMARY

One aspect is a filter module accommodating a filter having a shape that reduces leakage of a coolant.

Another aspect is a filter module including a sealing member having a shape that reduces leakage of a coolant.

Another aspect is a filter module accommodating a filter for filtering out impurities from a coolant emitted from a coolant storage unit, the filter module comprising: a filter accommodation member comprising a support surface formed in a plate shape, an accommodation surface located on an edge of the support surface and protruding in a first direction with respect to the support surface, and a perforating member located at a center of the support surface and protruding in a second direction with respect to the support surface; a first sealing member having a width smaller than a width defined by the accommodation surface so that disposed within the accommodation surface; a second sealing member comprising a through-hole having a width greater than a width defined by the perforating member so that the second sealing member is fitted into the perforating member; and a filter disposed between the first sealing member and the support surface; wherein the filter has a shape different from a shape defined by the accommodation member and has an area smaller than an area defined by the accommodation member such that the first sealing member has a contact surface with the support surface even when the filter is disposed in the filter accommodation member.

Another aspect is a a cooling device that performs cooling by spraying coolant to a target area, the cooling device comprising: a main body accommodating a nozzle that sprays coolant and a valve that control the flow to coolant; a coolant storage unit configured to store coolant; and a filter module comprising: a filter accommodation member comprising: a support surface formed in a plate shape, an accommodation surface located on an edge of the support surface and protruding in a first direction with respect to the support surface, and a perforating member located at a center of the support surface, protruding in a second direction with respect to the support surface; a first sealing member having a width smaller than a width defined by the accommodation surface so that disposed within the accommodation surface; a second sealing member comprising a through-hole having a width greater than a width defined by the perforating member so that the second sealing member is fitted into the perforating member; and a filter disposed between the first sealing member and the support surface; wherein the main body comprising a connecting member configured to couple to the filter accommodation member of the filter module, wherein the filter has a shape different from a shape defined by the accommodation member and has an area smaller than an area defined by the accommodation member such that the first sealing member has a contact surface with the support surface even when the filter is disposed in the filter accommodation member.

Another aspect is a filter module accommodating a filter for filtering out impurities from a coolant emitted from a cartridge comprising a cartridge housing and a cap, the filter module comprising: a filter accommodation member comprising a support surface formed in a plate shape, an accommodation surface located on an edge of the support surface and protruding in a first direction with respect to the support surface, and a perforating member located at a center of the support surface and protruding in a second direction with respect to the support surface; and a first sealing member having a first external diameter and comprising a through-hole having a width greater than a width defined by the perforating member so that the first sealing member is fitted into the perforating member, wherein, when the cap is connected by the perforating member, the first sealing member is transformed into a shape having a second external diameter corresponding to a width of an inlet of the housing accommodating the cap, and is inserted into the inside of the housing to press the cap, wherein the second external diameter is smaller than the first external diameter.

Another aspect is a cooling device that performs cooling by spraying coolant to a target area, the cooling device comprising: a cartridge comprising a cap preventing external leakage of the coolant and a housing that accommodates the cap inside and has a coupling member formed on the external surface and configured to store the coolant; a main body accommodating a nozzle that sprays coolant and a valve that control the flow to coolant and comprising a connecting member configured to couple with the coupling member of the cartridge; and a filter module comprising: a filter accommodation member comprising: a support surface formed in a plate shape, an accommodation surface located on an edge of the support surface and protruding in a first direction with respect to the support surface, and a perforating member located at a center of the support surface, protruding in a second direction with respect to the support surface and perforating the cap; and a first sealing member comprising a through-hole having a width greater than a width defined by the perforating member, fitted into the perforating member and having a first external diameter; wherein, when the cap is connected by the perforating member, the first sealing member is transformed into a shape having a second external diameter corresponding to a width of an inlet of the housing accommodating the cap, and is inserted into the inside of the housing to press the cap, wherein the second external diameter is smaller than the first external diameter.

Aspects of the present disclosure are not limited to the above-described aspects, and aspects not mentioned will be clearly understood by those skilled in the art to which the present disclosure pertains from this description and the accompanying drawings.

According to an exemplary embodiment of the present disclosure, leakage of a coolant accommodated in a cartridge may be minimized.

According to an exemplary embodiment of the present disclosure, external leakage of a coolant flowing from a coolant transfer unit may be minimized.

The effects according to the present disclosure are not limited to the effects described above, and the effects not mentioned may be clearly understood by those skilled in the art to which the present disclosure pertains from this description and the accompanying drawings.

BRIEF DESCRIPTION OF THE DRAWINGS

FIG. 10 is a table showing results of coolant leakage experiments.

FIG. 16 is a table showing results of coolant leakage experiments.

DETAILED DESCRIPTION

Figure 1:
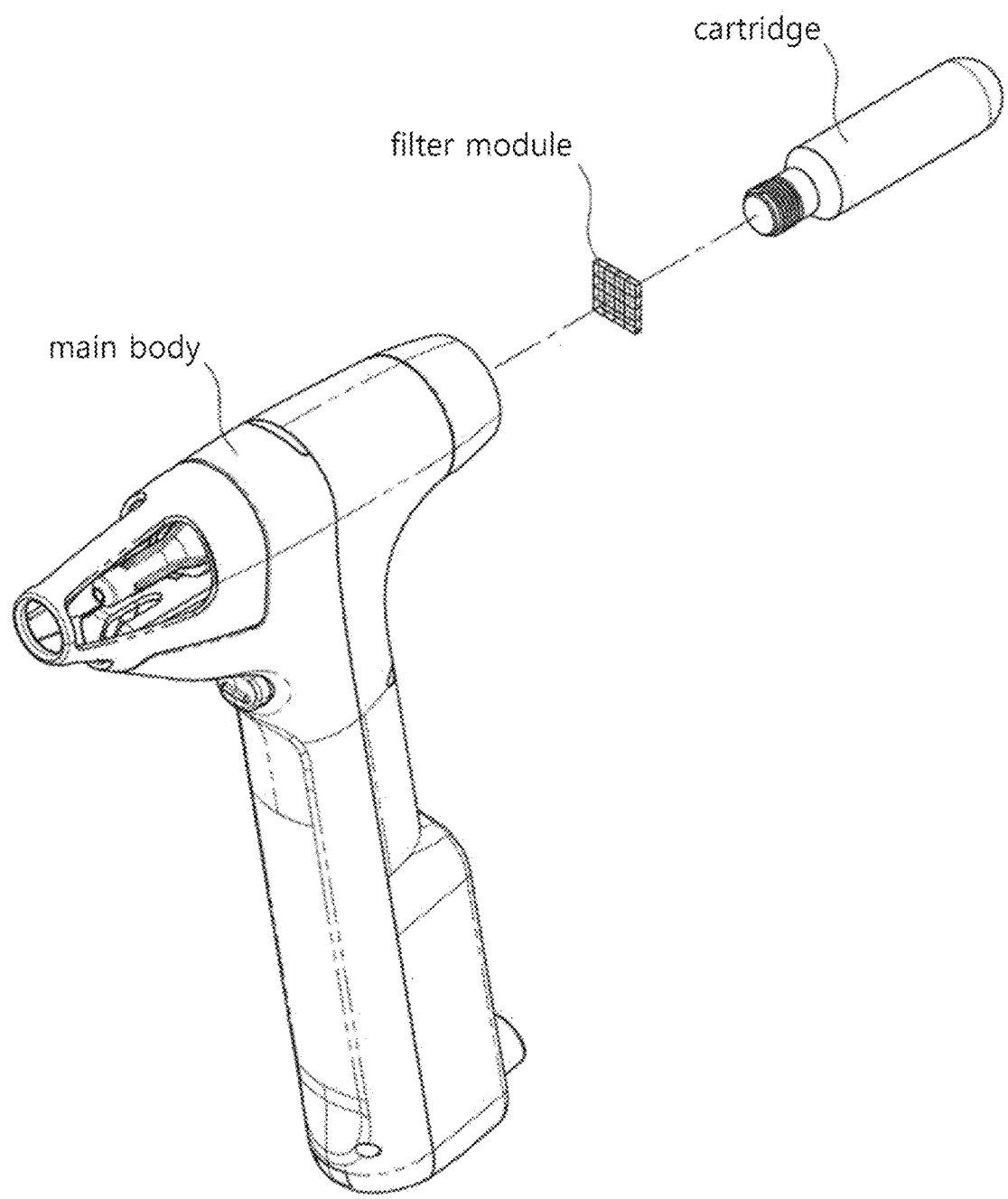
FIG. 1 is a schematic view showing a cooling device including a filter module according to an exemplary embodiment of the present disclosure.

Cooling devices using a variety of methods, such as contact methods, are being used or studied for cooling treatments and in particular cooling devices that cool treatment areas by spraying a coolant onto treatment areas have attracted attention.

However, cooling devices using a coolant spray method have a problem in that a coolant unnecessarily leaks to the outside not only when the cooling device is operating, but also when the operation of the cooling device is temporarily stopped.

In addition, a safety problem may be inevitably present in that cooling devices for skin treatments perform procedures on the skin. For example, impurities included in the coolant may be transferred to a target area of the skin, causing a problem in which the skin is infected.

Therefore, research is required on a structure of a cooling device that may perform cooling by securing safety while minimizing leakage of the coolant.

According to an embodiment of the present disclosure, A filter module accommodating a filter for filtering out impurities from a coolant emitted from a coolant storage unit, the filter module comprising: a filter accommodation member comprising a support surface formed in a plate shape, an accommodation surface located on an edge of the support surface and protruding in a first direction with respect to the support surface, and a perforating member located at a center of the support surface and protruding in a second direction with respect to the support surface; a first sealing member having a width smaller than a width defined by the accommodation surface so that disposed within the accommodation surface; a second sealing member comprising a through-hole having a width greater than a width defined by the perforating member so that the second sealing member is fitted into the perforating member; and a filter disposed between the first sealing member and the support surface; wherein the filter has a shape different from a shape defined by the accommodation member and has an area smaller than an area defined by the accommodation member such that the first sealing member has a contact surface with the support surface even when the filter is disposed in the filter accommodation member.

According to an embodiment of the present disclosure, the filter has a shape comprising a center part and at least one protrusion part extending outward from the center part, and when the filter is disposed in the filter accommodation member, the center part of the filter may be arranged to correspond to the flow path formed in the perforating member.

According to an embodiment of the present disclosure, an area of the center part of the filter may be larger than an area of a shape defined by the perforating member, but may be smaller than an area of a shape defined by the accommodation surface.

According to an embodiment of the present disclosure, the center of the filter may have a shape corresponding to a shape defined by the accommodation surface.

According to an embodiment of the present disclosure, the protrusion part includes a first foot and a second foot, wherein the first foot extends from a first internal end connected to the center part to a first external end not connected to the center part, wherein the second foot extends from a second internal end connected to the center part to a second external end not connected to the center part, wherein the first external end and the second external end may be spaced apart.

According to an embodiment of the present disclosure, a separation distance between the first external end and the second external end may be greater than a width of the center part.

According to an embodiment of the present disclosure, a separation distance between the first external end and the second external end may be greater than or equal to a width of a shape defined by the accommodation surface.

According to an embodiment of the present disclosure, when the filter is disposed within the filter accommodation member, each of the first external end and the second external end may contact the inner surface of the accommodation surface.

According to an embodiment of the present disclosure, the first foot has a shape in which a length of the first internal end is greater than a width of an area adjacent to the first external end, the second foot has a shape in which a length of the second internal end is greater than a width of an area adjacent to the second external end.

According to an embodiment of the present disclosure, the protrusion part may include a plurality of feet, from 2 or more but 6 of less, and the plurality of feet may be formed symmetrically with respect to the center part of the filter.

According to an embodiment of the present disclosure, a cooling device that performs cooling by spraying coolant to a target area, the cooling device comprising: a main body accommodating a nozzle that sprays coolant and a valve that control the flow to coolant; a coolant storage unit configured to store coolant; and a filter module comprising: a filter accommodation member comprising: a support surface formed in a plate shape, an accommodation surface located on an edge of the support surface and protruding in a first direction with respect to the support surface, and a perforating member located at a center of the support surface, protruding in a second direction with respect to the support surface; a first sealing member having a width smaller than a width defined by the accommodation surface so that disposed within the accommodation surface; a second sealing member comprising a through-hole having a width greater than a width defined by the perforating member so that the second sealing member is fitted into the perforating member; and a filter disposed between the first sealing member and the support surface; wherein the main body comprising a connecting member configured to couple to the filter accommodation member of the filter module, wherein the filter has a shape different from a shape defined by the accommodation member and has an area smaller than an area defined by the accommodation member such that the first sealing member has a contact surface with the support surface even when the filter is disposed in the filter accommodation member.

According to another embodiment of the present disclosure, a filter module accommodating a filter for filtering out impurities from a coolant emitted from a cartridge comprising a cartridge housing and a cap, the filter module comprising: a filter accommodation member comprising a support surface formed in a plate shape, an accommodation surface located on an edge of the support surface and protruding in a first direction with respect to the support surface, and a perforating member located at a center of the support surface and protruding in a second direction with respect to the support surface; and a first sealing member having a first external diameter and comprising a through-hole having a width greater than a width defined by the perforating member so that the first sealing member is fitted into the perforating member, wherein, when the cap is connected by the perforating member, the first sealing member is transformed into a shape having a second external diameter corresponding to a width of an inlet of the housing accommodating the cap, and is inserted into the inside of the housing to press the cap, wherein the second external diameter is smaller than the first external diameter.

According to another embodiment of the present disclosure, the first sealing member has a shape corresponding to a shape of the inlet of the housing.

According to another embodiment of the present disclosure, a length of the perforating member is greater than a height of the first sealing member so that when the first sealing member is fitted into the perforating member, the perforating member protrudes to the outside of the first sealing member.

According to another embodiment of the present disclosure, the filter module further comprises a second sealing member disposed inner side of the accommodation surface and having a third external diameter that is smaller than a width defined by the accommodation surface, wherein the filter is disposed between the second sealing member and the filter accommodation member.

According to another embodiment of the present disclosure, the first external diameter of the first sealing member is smaller than the third external diameter of the second sealing member.

According to another embodiment of the present disclosure, the first sealing member comprises Teflon or Nylon 6-6, the second sealing member comprises Teflon or Nylon 6-6

According to another embodiment of the present disclosure, a cooling device that performs cooling by spraying coolant to a target area, the cooling device comprising: a cartridge comprising a cap preventing external leakage of the coolant and a housing that accommodates the cap inside and has a coupling member formed on the external surface and configured to store the coolant; a main body accommodating a nozzle that sprays coolant and a valve that control the flow to coolant and comprising a connecting member configured to couple with the coupling member of the cartridge; and a filter module comprising: a filter accommodation member comprising: a support surface formed in a plate shape, an accommodation surface located on an edge of the support surface and protruding in a first direction with respect to the support surface, and a perforating member located at a center of the support surface, protruding in a second direction with respect to the support surface and perforating the cap; and a first sealing member comprising a through-hole having a width greater than a width defined by the perforating member, fitted into the perforating member and having a first external diameter; wherein, when the cap is connected by the perforating member, the first sealing member is transformed into a shape having a second external diameter corresponding to a width of an inlet of the housing accommodating the cap, and is inserted into the inside of the housing to press the cap, wherein the second external diameter is smaller than the first external diameter.

According to another embodiment of the present disclosure, the filter module is disposed between the cartridge and the main body, wherein the first sealing member is changed to a shape having the second external diameter by receiving pressure in a third direction perpendicular to the support surface and inserted into the inlet of the housing when the connecting member and the coupling member are fastened, wherein the first sealing member disposed at the inlet of the housing receives pressure in the third direction and extends in a fourth direction perpendicular to the third direction to seal the housing.

The above-described objectives, features and advantages of the present disclosure will become apparent from the following detailed description with reference to the accompanying drawings. However, the present disclosure is subject to a variety of modifications and may have many different exemplary embodiments, and certain exemplary embodiments are illustrated and described in detail below with reference to the drawings.

In the drawings, the thicknesses of layers and areas are exaggerated for clarity, and references to an element or layer being "on" or "above" another element or layer include both directly on top of another element or layer as well as with another layer or other component interposed in the middle. Throughout the disclosure, identical reference numerals generally refer to the same components. In addition, components having identical functions within the scope of the same idea shown in the drawings of each exemplary embodiment are described using the same reference numerals, and duplicate descriptions are hereby omitted.

When it is determined that a detailed description of a known function or configuration related to the present disclosure would unnecessarily obscure the essence of the present disclosure, the detailed description is omitted. In addition, numbers (e.g., first, second, etc.) used in the course of the description of the present disclosure are merely identifiers to distinguish one component from another.

Furthermore, the suffixes "module" and "unit" for components used in the following exemplary embodiments are given or used solely for ease of description and are not intended to have a distinct meaning or role in and of themselves.

In the following exemplary embodiments, the singular expression includes the plural unless the context clearly indicates otherwise.

In the following exemplary embodiments, the terms "including", "having", and the like imply the presence of the features or components described in the present disclosure and do not preclude the possibility of adding one or more other features or components.

In the drawings, components may be exaggerated or reduced in size for ease of explanations. For example, the size and thickness of each configuration shown in the drawings are arbitrary for purposes of explanations and do not necessarily limit the present disclosure as shown.

A particular sequence of processes may be performed differently than the order in which they are described when a certain exemplary embodiment may be alternatively implementable. For example, two processes described in succession may be performed substantially simultaneously or may be performed in the opposite order from that described.

In the following exemplary embodiments, when areas, components, and the like are said to be connected, this includes not only cases where the areas, components, and the like are directly connected, but also cases where the areas, components, and the like are indirectly connected by having other areas, components, and the like interposed between them.

Hereinafter, with reference to the drawings, a filter module including a filter and/or a sealing member according to a variety of exemplary embodiments of the present disclosure that may be used in a cooling device will be described in detail. In one example, the present disclosure may disclose exemplary embodiments of shapes of the filter. In another example, the present disclosure may disclose exemplary embodiments of a shape of the sealing member included in the filter module.

Figure 2:
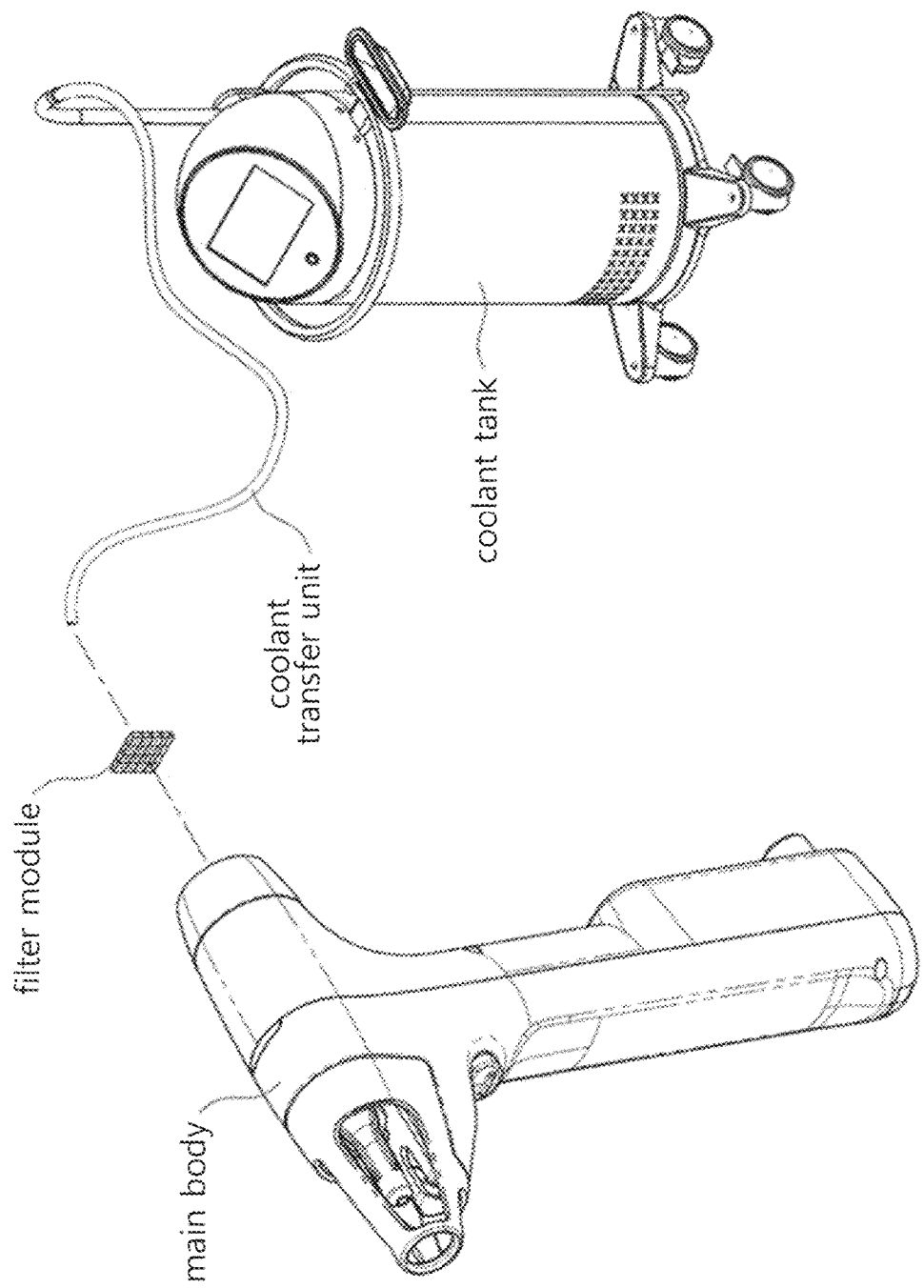
FIG. 2 is a schematic view showing a cooling system including a filter module according to an exemplary embodiment of the present disclosure.

FIG. 1 is a schematic view showing a cooling device including a filter module according to an exemplary embodiment of the present disclosure. FIG. 2 is a schematic view showing a cooling system including a filter module according to an exemplary embodiment of the present disclosure.

The cooling device may include a main body, a coolant storage unit, and a filter module.

The main body may be a handpiece type. Additionally, the main body may accommodate a nozzle that sprays a coolant and a valve that controls the flow of the coolant.

The coolant storage unit may be a cartridge type. Alternatively, the coolant storage unit may be a large type in the form of a coolant tank. When the coolant storage unit is in the form of the coolant tank, the coolant storage unit may further include a coolant transfer unit that transfers the coolant toward the main body. As an example, the coolant transfer unit may be provided in the form of a hose.

The cooling device may include the filter module for filtering out impurities in the coolant emitted from the coolant storage unit. As an example, the filter module may include a filter, an accommodation member for accommodating the filter, and at least one sealing member for preventing leakage of the coolant between other members connected to the filter module.

The filter module may be installed in the main body in any manner. As an example, the filter module may be disposed between the coolant storage unit and the main body. The filter module may further include a perforating member for perforating the coolant storage unit, so that the filter module may perforate the coolant storage unit to release the coolant when disposed (or installed) between the coolant storage unit and the main body. As an example, the filter module may include a through-hole that accommodates the coolant emitted from the coolant storage unit and transfers it to the main body. The coolant emitted from the coolant storage unit may be input into the main body via the filter module.

According to the conventional art, the filter for filtering impurities out of the coolant generally corresponds to the shape and size of an accommodation unit in which the filter is accommodated. Specifically, when the accommodation unit for the filter has a circular shape, the filter has been selected and used as a product having a circular shape. In this way, if the shape of the filter corresponds to the shape of the accommodation unit for the filter, there is a possibility that the coolant flowing into the filter may leak to the outside of the filter over all angular ranges without any difference, and in this case, it was found that the amount of leakage of the coolant stored in the coolant storage unit (e.g. cartridge) was relatively large.

The filter module according to exemplary embodiments of the present disclosure is designed to have a shape that minimizes leakage of the coolant. In one example, the filter disclosed in the present disclosure may be provided with a shape that is different from the shape of the filter accommodation member. In another example, the sealing member disclosed in the present disclosure may be provided in a shape that seals an opening of the coolant storage unit (e.g., an inlet of a housing) such that external leakage of the coolant emitted from the coolant storage unit is reduced.

Hereinafter, referring to FIGS. 3 to 16, the filter module that may be used in a variety of types of cooling devices as described above will be described in detail. Specifically, referring to FIGS. 3 to 11, described is the filter module that includes the filter having a shape that minimizes leakage of the coolant and the filter accommodation member that maximizes the sealing effect while accommodating the filter according to a first exemplary embodiment of the present disclosure. Also, referring to FIGS. 12 to 16, described is the filter module including the sealing member that has a shape to minimize leakage of the coolant according to a second exemplary embodiment of the present disclosure.

Figure 3:
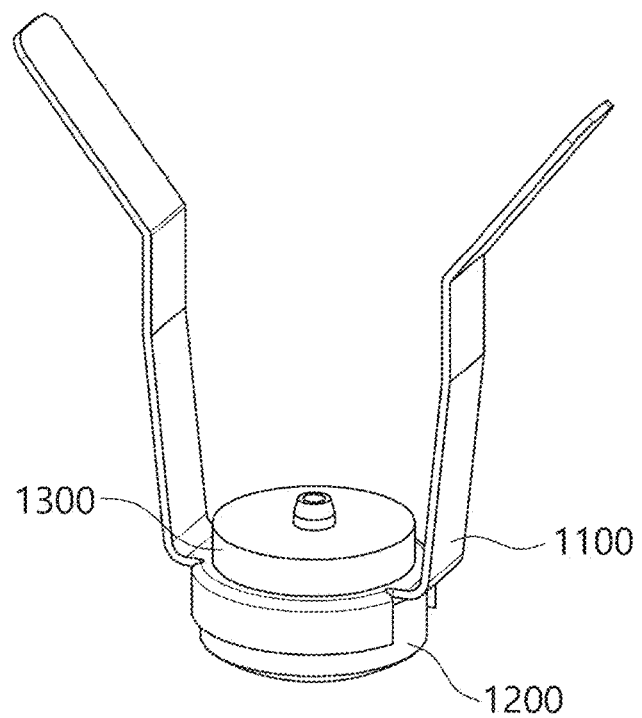
FIG. 3 is a view showing a filter module according to a first exemplary embodiment of the present disclosure.
Figure 4:
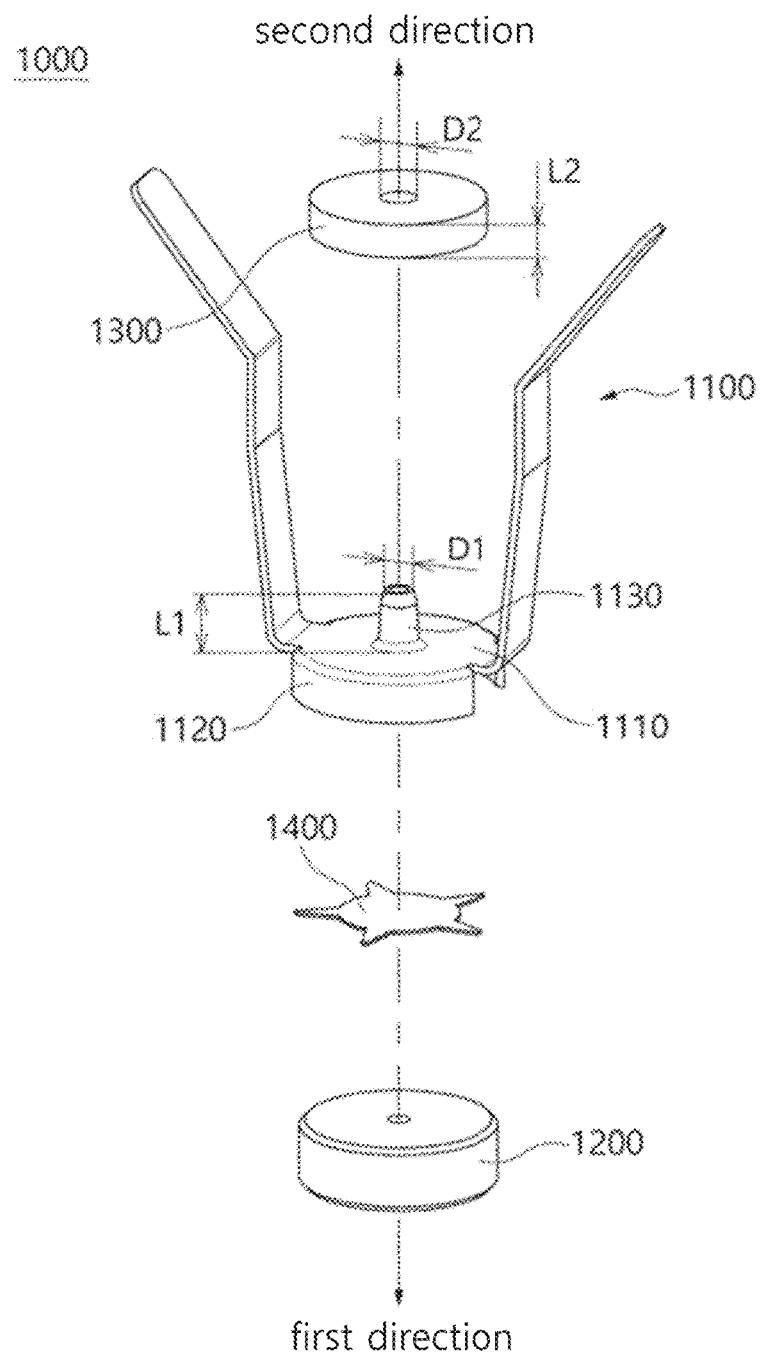
FIG. 4 is an exploded view of a filter module according to a first exemplary embodiment of the present disclosure.

Refer to FIGS. 3 and 4. FIG. 3 is a view showing a filter module according to the first exemplary embodiment of the present disclosure. FIG. 4 is an exploded view of a filter module according to the first exemplary embodiment of the present disclosure.

The filter module 1000 may include a filter accommodation member 1100, a first sealing member 1200, a second sealing member 1300, and a filter 1400 according to an exemplary embodiment of the present disclosure.

The filter accommodation member 1100 may include a support surface 1110, an accommodation surface 1120, and a perforating member 1130.

The support surface 1110 may be formed in a plate shape. For example, the support surface 1110 may be formed in a circular plate shape. The support surface 1110 may perform a function of supporting the filter 1400 accommodated in the filter accommodation member 1100.

The accommodation surface 1120 may be located at the edge of the support surface 1110 and may protrude in a first direction with respect to the support surface 1110. The accommodation surface 1120 may perform a function of accommodating the first sealing member 1200 and/or the filter 1400.

The perforating member 1130 may be located at a center of the support surface 1110. Additionally, the perforating member 1130 may protrude in a second direction with respect to the support surface 1110. At this time, the second direction may be opposite to the first direction in which the accommodation surface 1120 extends with respect to the support surface 1110. The perforating member 1130 may perform a function of inserting the second sealing member 1300 and perforating the coolant storage unit (e.g. cartridge). In addition, the perforating member 1130 has a flow path formed therein, and can perform a function of outputting the coolant emitted from the perforated coolant storage unit (e.g. cartridge) toward the filter 1400 of the filter module 1000 through the flow path formed therein.

The filter module 1000 according to an exemplary embodiment of the present disclosure may include at least one sealing member that performs a function of preventing leakage of the coolant. Specifically, the filter module 1000 may include the first sealing member 1200 and/or the second sealing member 1300.

As an example, the first sealing member 1200 may perform a function of preventing leakage of the coolant flowing into the main body. To this end, the first sealing member 1200 may be disposed between the main body and the filter module 1000. Specifically, the first sealing member 1200 may be disposed between the main body and the support surface 1110 of the filter module 1000. Alternatively, the first sealing member 1200 may be disposed between the main body and the filter 1400 of the filter module 1000. In addition, the first sealing member 1200 may be accommodated in the accommodation surface 1120 of the filter accommodation member 1100. In other words, the first sealing member 1200 may be accommodated in the accommodation surface 1120 extending in the first direction with respect to the support surface 1110. Through this structure, the first sealing member 1200 may perform a function of reducing leakage of the coolant flowing from the filter module 1000 to the main body of the cooling device.

As an example, the second sealing member 1300 may perform a function of preventing leakage of the coolant emitted from the coolant storage unit. To this end, the second sealing member 1300 may be disposed between the coolant storage unit and the filter module 1000. In other words, the second sealing member 1300 may be disposed in the second direction with respect to the support surface 1110. For a specific example, the filter module 1000 may include the perforating member 1130 extending in the second direction with respect to the support surface 1110. At this time, the second sealing member 1300 may include a through-hole having a width greater than the width defined by the perforating member 1130. Specifically, the internal diameter of the second sealing member 1300 defined by the through-hole of the second sealing member 1300 may be larger than the external diameter of the perforating member 1130. At this time, the second sealing member 1300 may be coupled to the filter accommodation member 1100 by fitting the through-hole of the second sealing member 1300 into the perforating member 1130. With this structure, the second sealing member 1200 may perform a function of reducing leakage of the coolant which flows from the coolant storage unit (e.g., cartridge or coolant tank) through the flow path formed inside the perforating member 1130 to the external surface of the perforating member 1130.

Meanwhile, the first sealing member 1200 may include a center-hollow hole through which a coolant may flow. For example, a center-hollow hole, a passageway through which the coolant may flow, may be formed in the center of the first sealing member 1200.

Additionally, the first sealing member 1200 may be composed of Teflon or Nylon 6 (Nylon 6-6). The second sealing member 1200 may also be composed of Teflon or Nylon 6 (Nylon 6-6).

The filter 1400 may be disposed within the filter accommodation member 1100. As an example, the filter 1400 may be disposed between the filter module 1000 and the main body. At this time, the filter 1400 may serve to filter out impurities contained in the coolant flowing from the filter module 1000 to the main body. For a specific example, the filter 1400 may be disposed between the support surface 1110 and the first sealing member 1200. At this time, the filter 1400 may serve to filter out impurities contained in the coolant which flows from the support surface 1110 to the first sealing member 1200. The shape and structure of the filter 1400 will be described in detail with reference to FIGS. 6 to 11.

The filter 1400 may be manufactured from a variety of materials. For example, the filter 1400 may be made of a variety of materials, including paper, metal, synthetic fibers, or polymeric compounds.

The filter 1400 may be disposable when the cooling device is used, and in this case, the material of the filter 1400 may include paper. By making the filter 1400 of paper material, the manufacturing cost of the filter 1400 may be relatively reduced, and the product manufacturing cost or the post-management cost may be reduced in that the filter 1400 has to be replaced with each use of the cooling device. When the filter 1400 is to be reused rather than a one-time use, the material of the filter 1400 may include a material other than paper material.

The filter 1400 may be implemented in the form of a mesh net. For example, the filter 1400 may be in the form of a mesh containing a plurality of pores with a predetermined size.

The filter 1400 may be implemented in a variety of shapes. For example, the filter 1400 may be implemented in a disk shape with a predetermined diameter and a circular cross-section, or in a disk shape with a predetermined width and a square cross-section. For another example, the filter 1400 may be implemented in a shape with protrusions, as described later.

Meanwhile, the filter module 1000 according to an exemplary embodiment of the present disclosure may further include a grip unit. The grip unit may include at least one grip member. At least one grip member may be accommodated in a connecting member of the main body. For example, a groove corresponding to the shape of the grip member may be formed in the connecting member of the main body, and the filter module 1000 may be mounted on the main body by accommodating the grip member in the groove formed in the connecting member of the main body. The filter module 1000 may be accommodated in the connecting member of the main body through the grip member, and the coolant storage unit may be more easily perforated by the perforating member 1130 of the filter module 1000 by being fastened to the connecting member of the main body that accommodates the filter module 1000, as described later.

Figure 5:
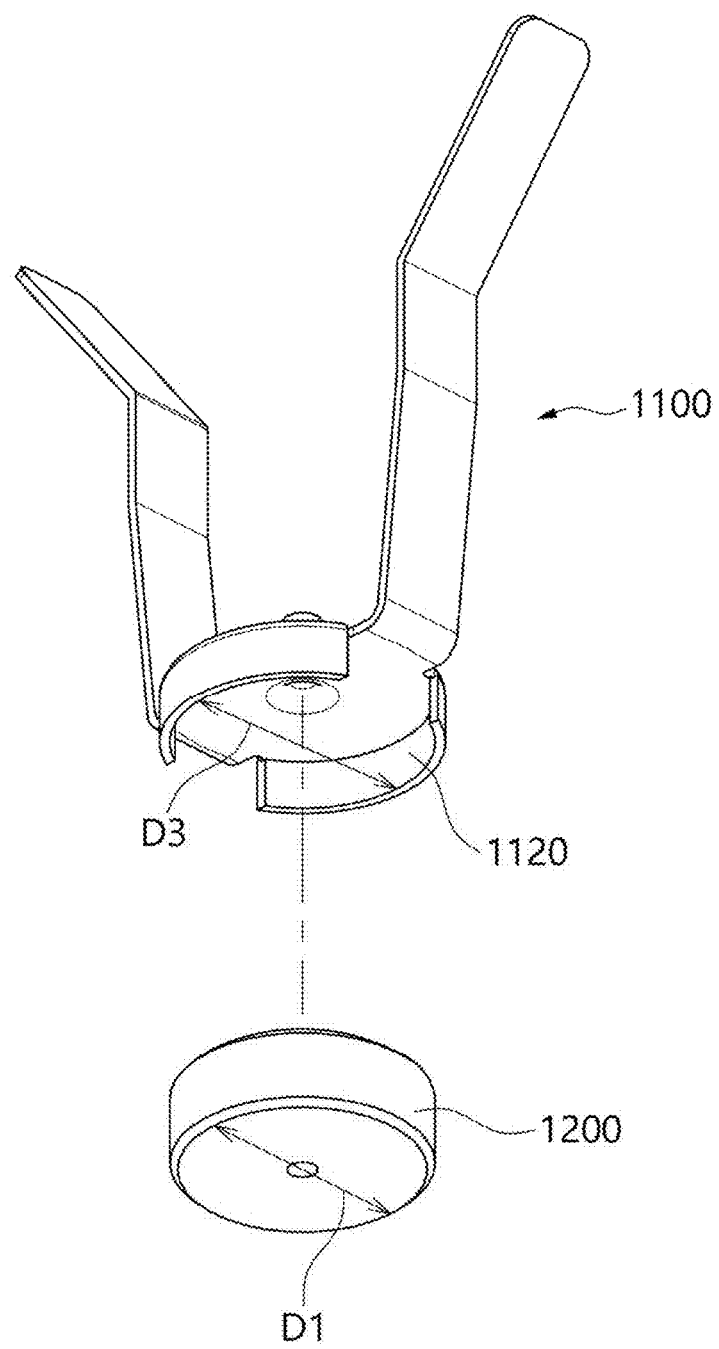
FIG. 5 is a view for explaining an aspect in which a first sealing member is accommodated in a filter accommodation member according to a first exemplary embodiment of the present disclosure.

Refer to FIG. 5. FIG. 5 is a view for explaining an aspect in which the first sealing member is accommodated in the filter accommodation member according to the first exemplary embodiment of the present disclosure.

The first sealing member 1200 may have a size corresponding to a width defined by the accommodation surface 1120. Herein, the width defined by the accommodation surface 1120 may mean a diameter of the shape defined by the accommodation surface 1120. Specifically, the width defined by the accommodation surface 1120 may be the length of the longest part of the shape defined by the accommodation surface 1120. For example, when the shape defined by the accommodation surface 1120 is circular, the width defined by the accommodation surface 1120 may be the diameter. In another example, when the shape defined by the accommodation surface 1120 is a quadrangle, the width defined by the accommodation surface 1120 may be a diagonal. In a specific example, the shape defined by the accommodation surface 1120 may be circular. In this case, the width defined by the accommodation surface 1120 may be a diameter D3 of the shape of the circle defined by the accommodation surface 1120. The first sealing member 1200 according to an exemplary embodiment of the present disclosure may have an external diameter D4 that is less than or less than the width D3 defined by the accommodation surface 1120.

In addition, the first sealing member 1200 may have a shape corresponding to the shape of the accommodation surface 1120. For example, when the shape defined by the accommodation surface 1120 is circular, the first sealing member 1200 may be provided in a circular shape corresponding to the shape defined by the accommodation surface 1120. For example, when the shape defined by the accommodation surface 1120 is quadrangle, the first sealing member 1200 may be provided in a quadrangle shape corresponding to the shape defined by the accommodation surface 1120.

Through this, at least a part of the first sealing member 1200 may be accommodated in the filter accommodation member 1100 by the accommodation surface 1120.

However, the shape and size of the accommodation surface and the shape and size of the first sealing member shown in FIG. 5 are only examples and may be transformed into a structure having any suitable shape and size to achieve the purpose of the filter module which filters out impurities in the coolant emitted from the coolant storage unit and prevents leakage of the coolant while outputting the filtered coolant in the direction of the main body.

As described above, the second sealing member 1300 according to an exemplary embodiment of the present disclosure may be fitted into the perforating member 1130 of the filter accommodation member 1100. Referring to FIG. 4 again, the second sealing member 1300 may include a through-hole formed in the center of the second sealing member 1300. In this case, a width D2 of the through-hole of the second sealing member 1300 may be greater than or equal to a width D1 defined by the perforating member 1130. Through this, the second sealing member 1300 may be fitted into the perforating member 1130 of the filter accommodation member 1100, and reduced may be leakage of the coolant that flows from the coolant storage unit (e.g., cartridge or coolant tank) into the inner flow path of the perforating member 1130 to the external surface of the perforating member 1130.

Additionally, a height (or thickness, L2) of the second sealing member 1300 may be smaller than a length L1 of the perforating member 1130. Through this, even when the second sealing member 1300 is fitted into the perforating member 1130, the perforating member 1130 may protrude to the outside of the second sealing member 1300. Accordingly provided may be a structure in which the perforating member 1130 protruding outside perforates the coolant storage unit (e.g., a hose connected to a cartridge or the coolant tank). Additionally, the coolant emitted from the coolant storage unit may flow into the filter 1400 disposed within the filter accommodation member 1110.

The filter may have the same shape as the shape of the support surface 1110.

According to an exemplary embodiment of the present disclosure, the filter 1400 may have a shape different from the shape of the support surface 1110.

Hereinafter, the shape and characteristic of the filter 1400 according to an exemplary embodiment of the present disclosure will be described in detail with reference to FIGS. 6 to 9.

Figure 6:
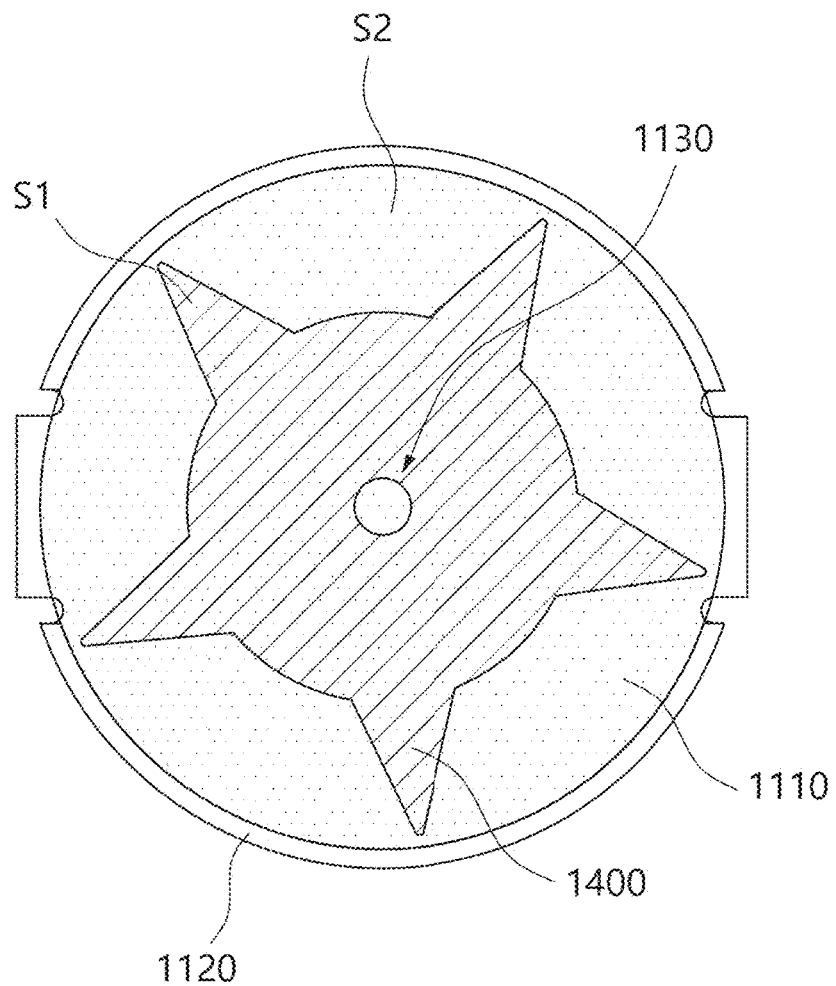
FIG. 6 is a view showing an aspect in which a filter according to a first exemplary embodiment of the present disclosure is accommodated in a filter accommodation member.

Refer to FIG. 6. FIG. 6 is a view showing an aspect in which the filter 1400 according to the first exemplary embodiment of the present disclosure is accommodated in the filter accommodation member 1110.

The filter 1400 according to an exemplary embodiment of the present disclosure may be disposed within the filter accommodation member 1100. At this time, the filter 1400 may accommodate the coolant flowing in from the flow path formed in the perforating member 1130 and filter out impurities in the accommodated coolant, thereby ensuring the safety of the cooling device.

According to an exemplary embodiment of the present disclosure, the filter 1400 may have a shape different from a shape defined by the accommodation surface 1120 such that the first sealing member 1200 has a contact surface with the support surface 1100 when the filter 1400 is disposed on the filter accommodation member 1100. In addition, even when the filter 1400 is disposed within the filter accommodation member 1100, the filter 1400 may have a shape with an area S1 smaller than an area S2 defined by the accommodation surface 1120 so that the first sealing member 1200 may have a contact surface with the support surface 1100. Accordingly, leakage of the coolant may be further prevented as the contact surface between the first sealing member 1200 and the support surface 1100 may be increased.

For a more specific example, the filter 1400 may be implemented in a form including a center part and a protrusion part including at least one foot so that the first sealing member 1200 may have a contact surface with the support surface 1110 even when the filter 1400 is disposed within the filter accommodation member 1100. A detailed description of this will be given through FIGS. 7 and 8. This type of filter 1400 forms a contact surface between the first sealing member 1200 and the support surface 1110 at a radial position with respect to the center surface of the filter 1400, thereby preventing leakage of the coolant.

According to an exemplary embodiment of the present disclosure, the filter 1400 may be provided in a structure with any suitable shape and size so that the filter 1400 disposed in correspondence with the flow path formed in the perforating member 1130 when being disposed within the filter accommodation member 1100. For example, the width of the center part of the filter 1400 may be larger than the width of the flow path formed in the perforating member 1130. For example, the width of the center part of the filter 1400 may be smaller than the width of the shape defined by the accommodation surface 1120. In addition, when the filter 1400 is disposed on the filter accommodation member 1100, at least one foot of the protrusion part of the filter 1400 may contact the accommodation surface 1120 so that the movement of the filter 1400 may be limited. A detailed description of this will be made through FIG. 9. In this type of filter 1400, when the filter 1400 is disposed on the filter accommodation member 1100, the center part of the filter 1400 is located at a position corresponding to the flow path of the perforating member 1130 and prevents the filter 1400 from shaking, so impurities contained in the coolant flowing from the flow path of the perforating member 1130 may be removed by the filter 1400.

Figure 7:
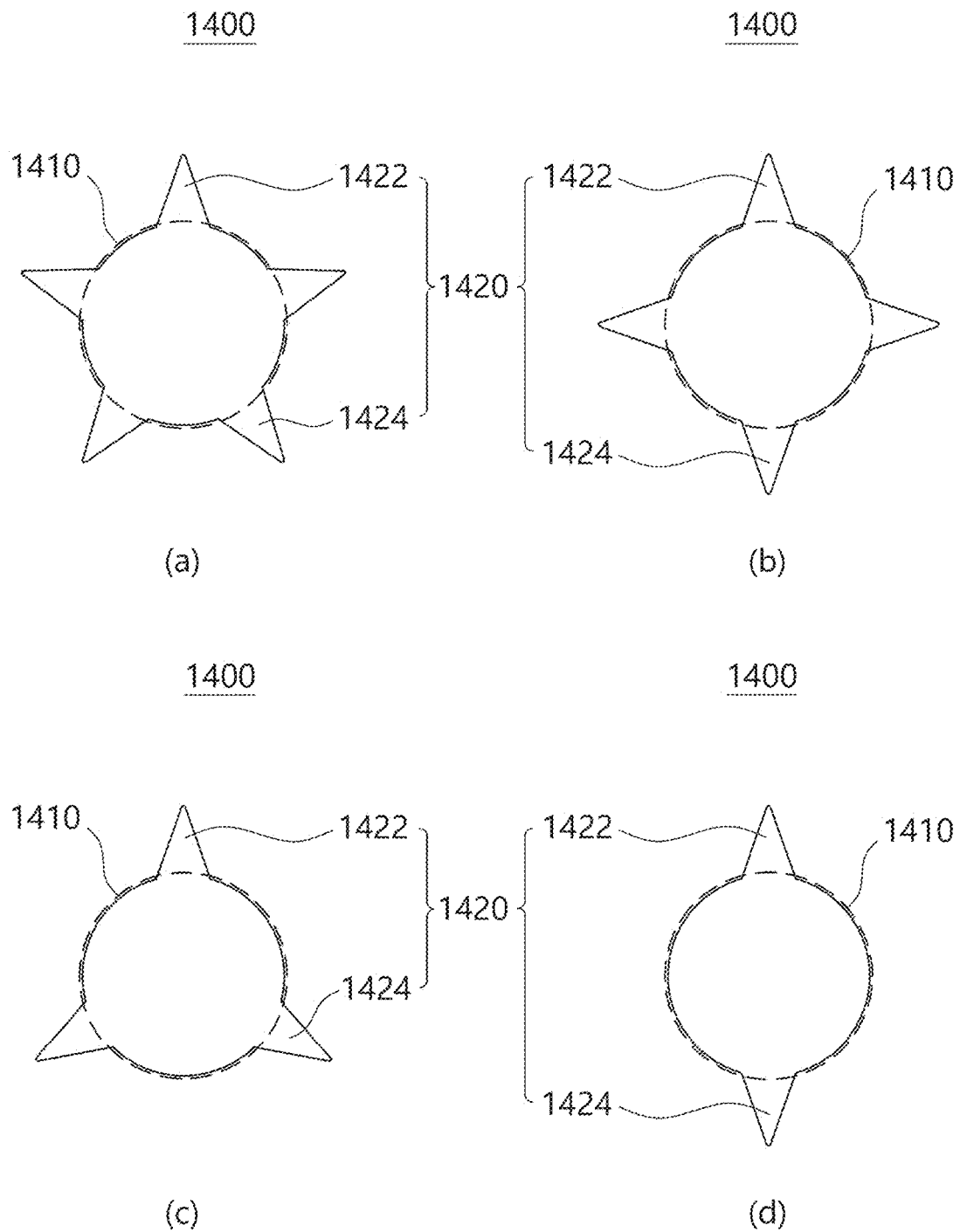
FIG. 7 is a view showing a variety of shapes of a filter according to a first exemplary embodiment of the present disclosure.
Figure 8:
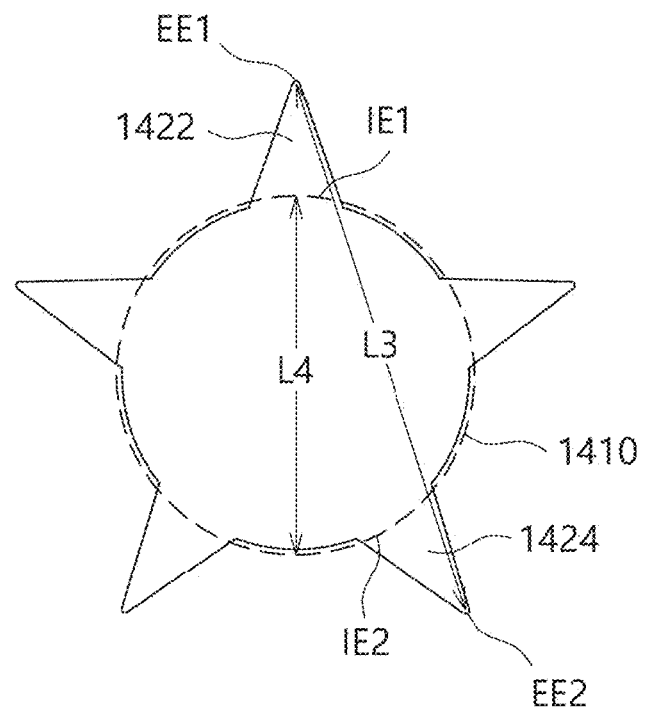
FIG. 8 is a view for explaining in more detail a shape of a filter according to a first exemplary embodiment of the present disclosure.
Figure 8:
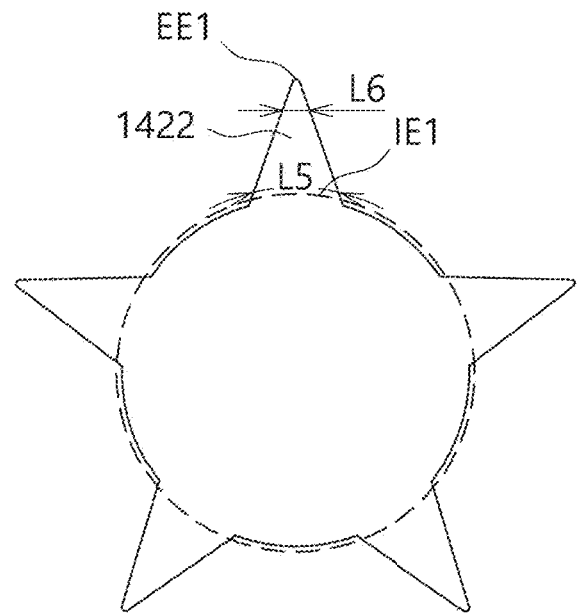

Hereinafter, features of the shape and size of the filter 1400 according to a variety of exemplary embodiments of the present disclosure will be described in detail with reference to FIGS. 7 and 8. FIG. 7 is a view showing a variety of shapes of the filter 1400 according to the first exemplary embodiment of the present disclosure. FIG. 8 is a view for explaining a shape of the filter 1400 in more detail according to the first exemplary embodiment of the present disclosure.

The filter 1400 according to an exemplary embodiment of the present disclosure may have a shape including a center part 1410 and at least one protrusion part 1420 extending outside from the center part 1410.

The center part 1410 of the filter 1400 may have a shape corresponding to the shape defined by the accommodation surface 1120. For example, the shape defined by the accommodation surface 1120 may be circular. At this time, the center part 1410 of the filter 1400 may be provided in a circular shape.

The area of the center part 1410 of the filter 1400 may be smaller than the area of the shape defined by the accommodation surface 1220. Through this, even when the filter 1400 is disposed within the filter accommodation member 1100 as described above, the first sealing member 1200 may have a contact surface with the support surface 1110.

On the other hand, the area of the center part 1410 of the filter 1400 may be greater than or equal to the area of the shape defined by the perforating member 1130. Through this, the filter 1400 may accommodate the coolant flowing from the flow path formed in the perforating member 1130 and filter out impurities in the coolant.

The protrusion part 1420 of the filter 1400 may include N feet. As used herein, a foot may encompass any structure with any shape and length extending toward the outside from the center part 1410 of the filter 1400.

The protrusion part 1420 of the filter 1400 according to an exemplary embodiment of the present disclosure may include two or more feet including a first foot 1422 and a second foot 1424. For example, the protrusion part 1420 of the filter 1400 may include 2 or more but 10 or less feet. In another example, the protrusion part 1420 of the filter 1400 may include 2 or more but 8 or less feet. In another example, the protrusion part 1420 of the filter 1400 may include 2 or more and 6 or less feet.

Meanwhile, multiple feet of the protrusion part 1420 of the filter 1400 according to an exemplary embodiment of the present disclosure may be formed symmetrically respect to the center part 1410 of the filter 1400.

The first foot 1422 may extend from a first internal end IE1 connected to the center part 1410 to a first external end EE1 that is not connected to the center part 1410. Similarly, the second foot 1424 may extend from a second internal end IE2 connected to the center part 1410 to a second external end EE2 that is not connected to the center part 1410. At this time, the first external end EE1 of the first foot and the second external end EE2 may be spaced apart from each other. Herein the internal end may mean encompassing an end included in any area of the protrusion part of the filter adjacent to or connected to the center part. Additionally, the external end may mean encompassing the end of the protrusion part that is spaced apart furthest away from the center part.

The filter 1400 according to one exemplary embodiment of the present disclosure may be formed in a structure in which a separation distance (L3 in FIG. 8) between the first external end EE1 of the first foot 1422 and the second external end EE2 of the second foot 1424 is greater than a width (L4 in FIG. 8) of the center part. With such a shape of the filter 1400, the effectiveness of preventing leakage of the coolant may be increased since the protrusion part 1420 of the filter 1400 may be in contact with and less shaken.

In addition, the first foot 1422 may have a shape in which a length (L5 in FIG. 8) of the first internal end IE1 is larger than a width of the area (L6 in FIG. 8) adjacent to the first external end EEL Similarly, the second foot 1424 may have a shape in which the length of the second internal end IE2 is greater than the width of the area adjacent to the second external end EE2. In other words, the first foot 1422 and/or the second foot 1424 may have a shape that becomes thinner and thinner toward the outside from the center part 1410. With this shape, the filter 1400 may have an area smaller than the area of the shape defined by the accommodation surface 1120. Also, when the filter 1400 is disposed between the first sealing member 1200 and the support surface 1110, a contact surface may be formed where the first sealing member 1200 is in contact with the support surface 1110. Accordingly, the area where the first sealing member 1200 seals the outside of the filter 1400 is increased, thereby providing the effect of minimizing leakage of the coolant.

Figure 9:
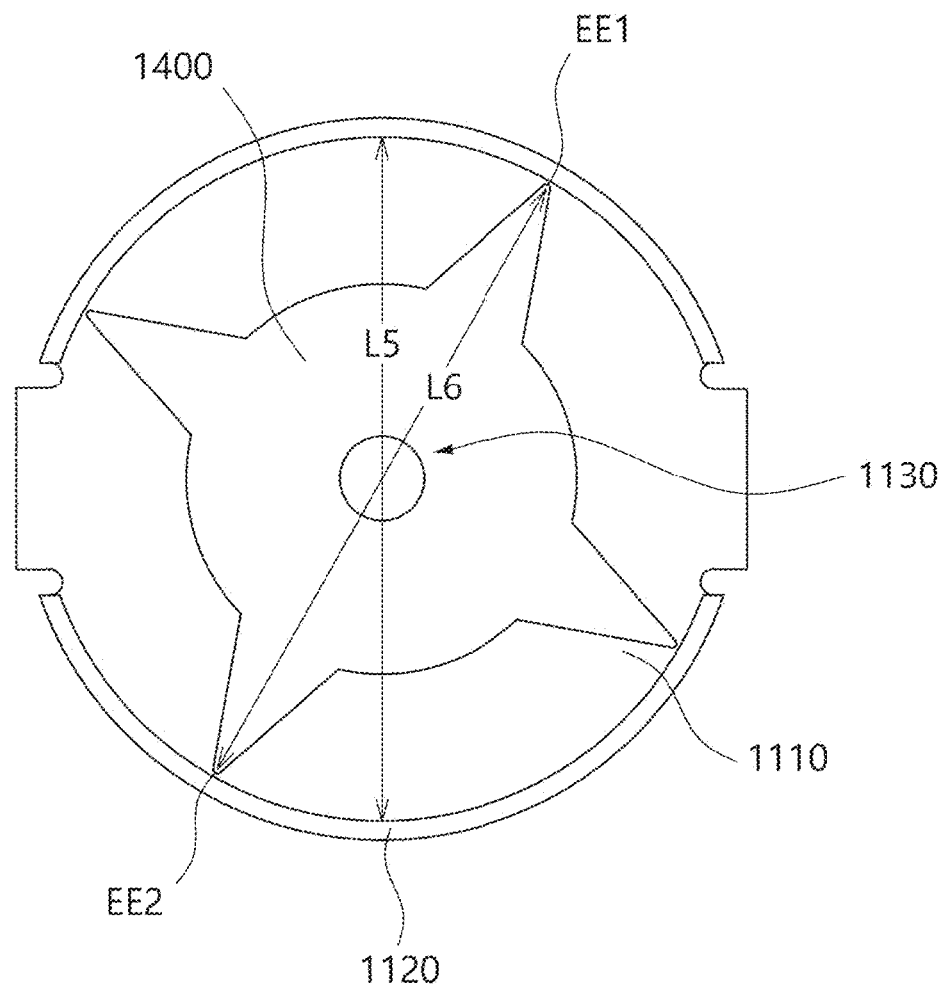
FIG. 9 is a view for explaining in more detail a shape of a filter according to a first exemplary embodiment of the present disclosure.

Refer to FIG. 9. FIG. 9 is a view for more specifically explaining the shape of the filter 1400 according to the first exemplary embodiment of the present disclosure.

The filter 1400 may include a center part 1410 and at least one protrusion part 1420 extending toward outside from the center part 1410 as described above. At this time, the protrusion part 1420 may include the first foot 1422 and the second foot 1424.

Herein, a separation distance L6 between the first external end EE1 of the first foot 1422 and the second external end EE2 of the second foot 1424 may be greater than or equal to the width L5 of the shape defined by the accommodation surface 1120. Through this, when the filter 1400 is disposed within the filter accommodation member 1100 (e.g., when disposed between the first sealing member 1200 and the support surface 1120), each of the first external end EE1 of the first foot 1422 and the second external end EE2 of the second foot 1424 may come in contact with an internal surface of the accommodation surface 1120. Thus, when the filter 1400 is disposed within the filter accommodation member 1110, the center part 1410 of the filter 1400 is located at a position corresponding to the position in which the coolant flow path of the perforating member 1130 is formed and the movement of the filter may be limited. This allows impurities in the coolant flowing in through the perforating member 1130 to be filtered out while minimizing leakage of the coolant.

The filter module 1000 according to an exemplary embodiment of the present disclosure has a contact surface between the first sealing member 1200 and the support surface 1110 due to the structure of the filter module 1000 and the shape of the filter 1400 described above. Accordingly, the first sealing member 1200 may seal the outside of the filter 1400, and leakage of the coolant to the outside through the filter 1400 may be prevented.

Hereinafter, referring to FIGS. 10 and 11, an experiment will be described in detail in order to prove the effectiveness of preventing leakage of the coolant of the filter module 1000 including the filter 1400 according to an exemplary embodiment of the present disclosure.

COMPARISON EXPERIMENT OF THE COOLANT LEAKAGE

Experimental Example

As an experimental example, prepared was a cartridge equipped with the filter module 1000 in which the filter 1400 is disposed within the filter accommodation member 1100 according to an exemplary embodiment of the present disclosure. Specifically, used was the filter module 1000 in which the filter with five feet was disposed within the filter accommodation member 1100. For the experimental group, a coolant leakage experiment was conducted on the cartridges of two different capacities (74 g, 45 g).

Comparative Example

As a comparative example, prepared was a cartridge equipped with the filter module 1000 in which a circular filter was disposed within the filter accommodation member 1100. Specifically, used was a circular filter having an area substantially equal to the area defined by the accommodation surface 1120 of the filter accommodation member 1100. For the comparison group, a coolant leakage experiment was conducted on a 74 g cartridge.

Experimental Method

The weight of the cartridge over time was measured by applying the same fastening force to the cartridge equipped with the filter module respectively prepared according to the comparative example and the experimental example. Additionally, the coolant consumption of the cartridge, that is, the coolant leakage amount, was measured based on the initial cartridge weight and the weight of the cartridge over time.

Experimental Results

FIG. 10 is a table showing the results of the coolant leakage experiments. Referring to FIG. 10, when the circular filter was disposed within the filter module 1000, the weight of the cartridge was initially measured to be 74 g, but when 24 hours elapsed, the weight of the cartridge was measured to be 0 g. That is, after 24 hours, the coolant stored in the cartridge was completely consumed in the case of the circular filter.

On the other hand, when the filter including multiple feet was disposed within the filter module 1000 according to an exemplary embodiment of the present disclosure, the weight of the cartridge was initially measured to be 74 g, 73.0 g when 24 hours elapsed, 72.6 g when 48 hours elapsed, and 72.4 g when 72 hours elapsed, and 72.3 g when 96 hours elapsed. In other words, it was confirmed that the coolant stored in the cartridge leaked less than 1 g even after 96 hours had elapsed in the case of the filter having multiple feet.

In addition, even when the experiment was conducted on other weight (45 g) cartridges, the weight of the cartridge was measured to be 44.8 g after 24 hours, 42.8 g after 48 hours, 36.6 g after 72 hours, and 33.8 g after 96 hours. In other words, it was confirmed that less than 5% of the coolant stored in the cartridge leaked even after 96 hours in the case of the filter having multiple feet.

Through the results of this experiment, it could be proven that the effect of preventing the coolant leakage is significantly improved when using the filter according to an exemplary embodiment of the present disclosure compared to using a conventional circular filter.

Experimental Analysis

Figure 11:
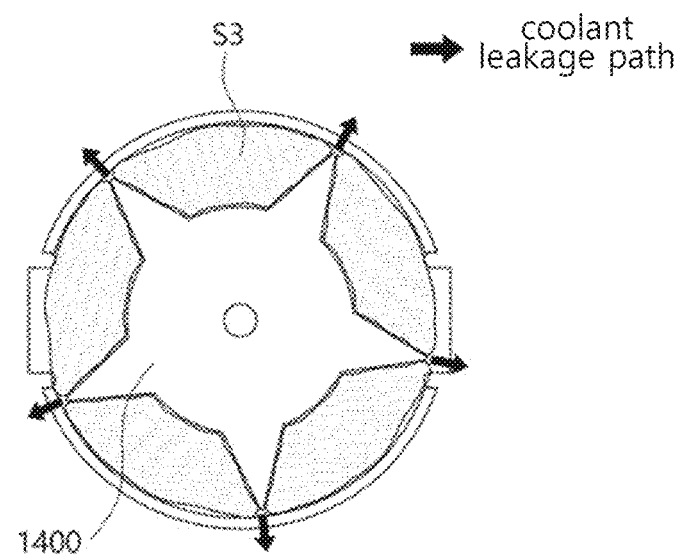
FIG. 11 is a view showing a leak path of a coolant to explain a cause of a significant difference in results of coolant leak comparison experiments of FIG. 10.
Figure 11:
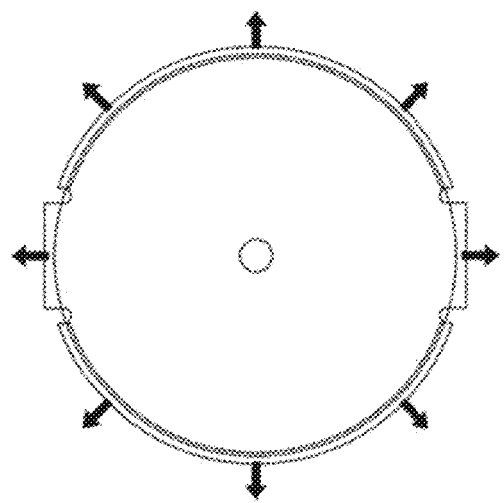

Refer to FIG. 11. FIG. 11 is a view schematically showing a leakage path of a coolant in order to explain a cause of a significant difference in the results of the coolant leakage comparison experiments in FIG. 10.

In the case of the comparative example, that is, when a conventional circular filter is accommodated in the filter accommodation member 1100, the first sealing member 1200 does not have a contact surface with the support surface 1110, and thus the effectiveness of the first sealing member 1200 in sealing an outer area of the circular filter may be significantly reduced. Accordingly, the coolant likely leaks through the filter to the outside of the filter module 1000 for all angle ranges.

On the other hand, in the case of the experimental example, that is, when the filter 1400 having multiple feet is accommodated in the filter accommodation member 1100 according to an exemplary embodiment of the present description, the first sealing member 1200 has a contact surface S3 with the support surface 1110 such that the first sealing member 1200 may seal the outer area of the filter 1400. Thus, the possibility of a coolant leaking to the outside of the filter module 1000 through the filter is significantly reduced.

Meanwhile, referring to FIG. 11, the accommodation surface 1120 may be formed only on a part of the edge of the support surface 1110. In this case, it may be more advantageous that at least one foot of the protrusion part 1420 which includes the first foot 1422 and the second foot 1424 of the filter 1400 may come in contact with the accommodation surface in order to limit the movement of the filter and position the center part of the filter to correspond to the flow path of the perforating member.

In FIGS. 3 to 11, the description focuses on the filter module in which the filter including multiple feet is accommodated. However, the shape of the filter or the structure of the filter module shown in FIGS. 3 to 11 is only an example for the convenience of explanation, and provided are filter and filter module which are transformed into a suitable structure for filtering out impurities in the coolant while preventing external leakage of the coolant by increasing the contact area between the first sealing member 1200 and the support surface 1110, and the scope of the rights of the present disclosure herein should be determined by the interpretation of the present claim.

Hereinafter, a filter module 2000 according to a second exemplary embodiment of the present disclosure will be described in detail with reference to FIGS. 12 to 16. In this exemplary embodiment, the description may focus on characteristics of the shape and size of a second sealing member 2300 that improves the leakage prevention effect of a coolant. Since the contents of the above-described filter accommodation member 1100, the first sealing member 1200, and the filter 1400 may be applied in the same way, thus overlapping contents will be omitted.

Figure 12:
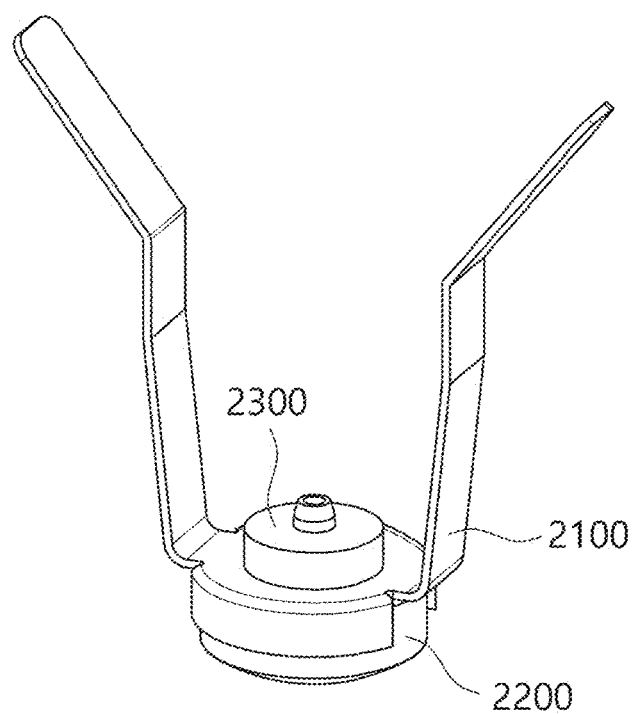
FIG. 12 is a view showing a filter module according to a second exemplary embodiment of the present disclosure.
Figure 13:
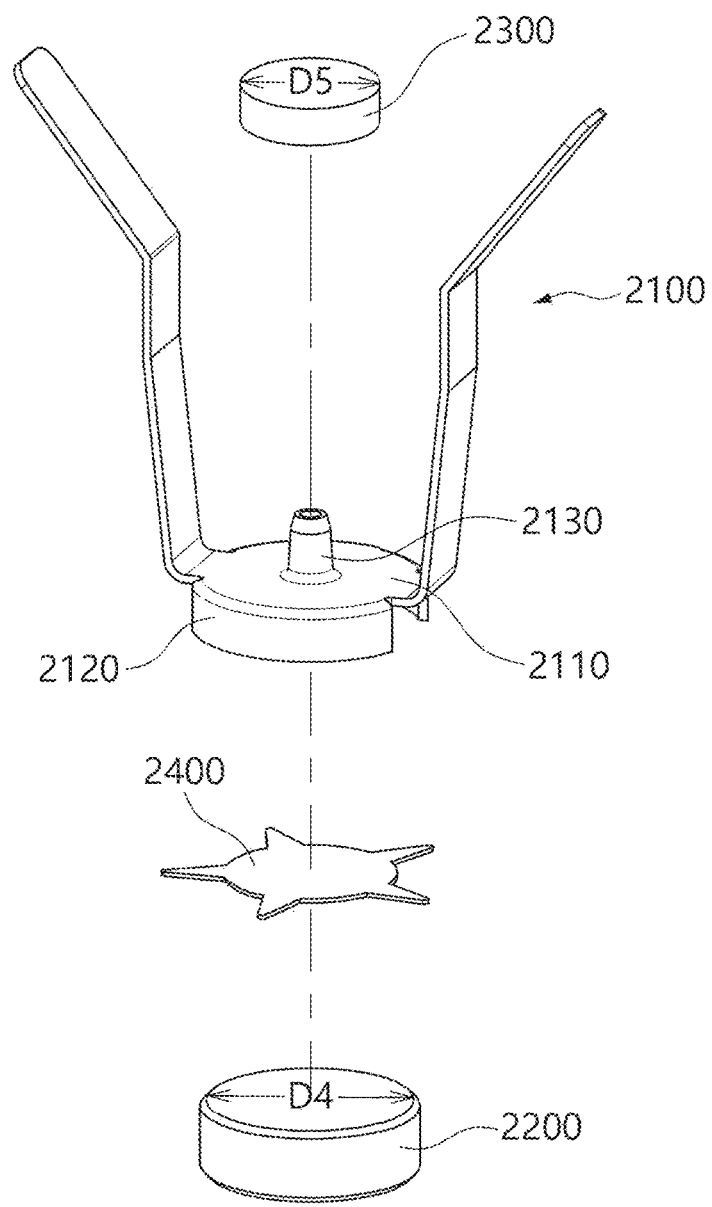
FIG. 13 is an exploded view of a filter module according to a second exemplary embodiment of the present disclosure.

Refer to FIGS. 12 and 13. FIG. 12 is a view showing a filter module according to the second exemplary embodiment of the present disclosure. FIG. 13 is an exploded view of a filter module according to the second exemplary embodiment of the present disclosure.

The filter module 2000 according to the second exemplary embodiment of the present disclosure may include a filter accommodation member 2100, a first sealing member 2200, a second sealing member 2300, and a filter 2400. Herein the filter accommodation member 2100 may be equally applied by the contents of the filter accommodation member 1100 of the filter module 1000 according to the above-described first exemplary embodiment. Additionally, the first sealing member 2200 may be equally applied by the contents of the first sealing member 1200 of the filter module 1000 according to the above-described first exemplary embodiment. Additionally, the filter 2400 may be equally applied by the contents of the filter 1400 of the filter module 1000 according to the above-described first exemplary embodiment. Meanwhile, in this exemplary embodiment, the filter the filter having a same shape as a shape defined by the accommodation surface (e.g., circular) may also be used.

The contents of the second sealing member 1300 according to the first exemplary embodiment described above may be inferred and applied to the second sealing member 2300 of the filter module 2000 according to the second exemplary embodiment of the present disclosure. However, the size and shape of the second sealing member 2300 according to the second exemplary embodiment of the present disclosure may be different from the second sealing member 1300 according to the first exemplary embodiment described above.

Specifically, an external diameter D5 of the second sealing member 2300 may have a shape smaller than the external diameter D4 of the first sealing member 2200. This may improve the sealing effect of an inlet of a cartridge housing by easily transforming the second sealing member 2300 to the external diameter corresponding to the width defined by the inlet of the cartridge housing when the perforating member 2130 perforates the coolant storage unit (e.g. cartridge) as described later.

Hereinafter, referring to FIGS. 14 to 16, the coupling relationship between the second sealing member 2300 and a coolant storage unit according to this exemplary embodiment will be described in detail. The following description will focus on a cartridge type as the coolant storage unit. However, this is only for the convenience of explanation, and the second sealing member 2300 may have any suitable shape and size in order to have the external diameter corresponding to the width of the coolant transfer unit (e.g. a hose) even when the second sealing member 2300 is coupled with the coolant transfer unit (e.g., a hose) of the coolant storage unit of a coolant tank type.

Figure 14:
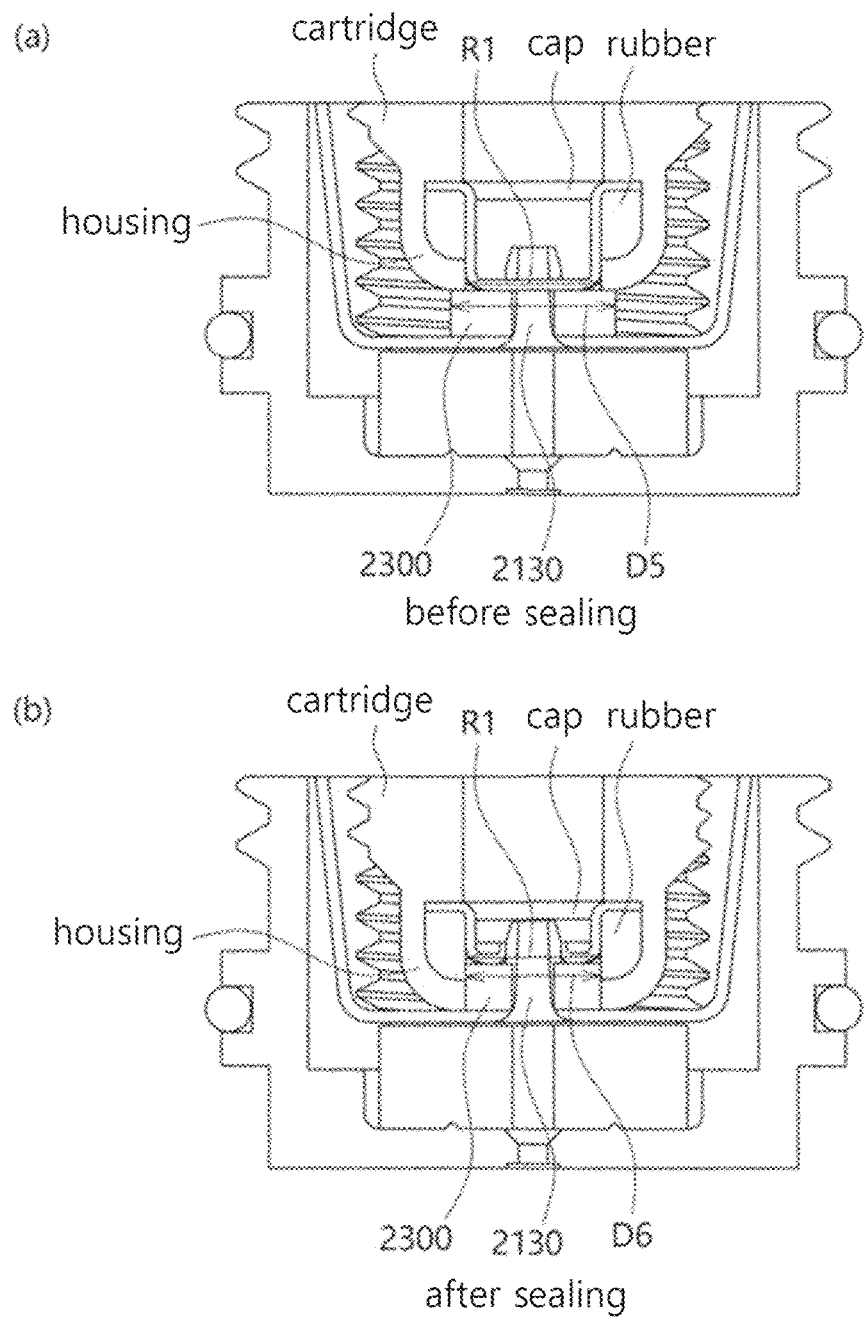
FIG. 14 is a view showing a cross-section of a second sealing member and a cartridge after the cartridge and a main body are fastened according to a second exemplary embodiment.

FIG. 14 is a view showing a cross-section of the second sealing member 2300 and a cartridge after the cartridge and a main body are fastened according to the second exemplary embodiment. Specifically, (a) of FIG. 14 is a view showing a cross-section of the second sealing member 2300 and the cartridge at the point when the cartridge begins to be fastened to the main body. (b) of FIG. 14 is a view showing a cross-section of the second sealing member 2300 and the cartridge at the point when the cartridge and the main body are completely fastened.

The cartridge may include a housing in which the coolant is stored and a cap that seals the coolant and is disposed adjacent to the inlet of the housing. The housing may be provided in a form that may accommodate the cap.

Herein the cap may be implemented as a material that is perforated by the perforating member as described later. For example, the material of the cap may be brass or stainless steel.

The cartridge may further include a rubber sealing the area between the cap and the housing, and the housing may be provided in a form that may accommodate the rubber. Meanwhile, a coupling member may be formed on the external surface of the housing, and the coupling member may be fastened to the connecting member formed on the main body of the cooling device. For example, the coupling member and the connecting member are configured with corresponding screw lines so that the cartridge and the main body may be fastened by screwing the cartridge to the main body. At this time, the filter module 2000 is disposed between the cartridge and the main body, filters out impurities in the coolant emitted from the cartridge, and outputs the coolant from which the impurities have been filtered to the main body.

The second sealing member 2300 according to this exemplary embodiment may have a width corresponding to the inlet of the cartridge housing. The second sealing member 2300 may have a width larger than the inlet of the cartridge housing by a predetermined length so as to be fitted into the inlet of the cartridge housing. Preferably, the predetermined length may be 2.5 mm or less. More preferably, the predetermined length may be 1.5 mm or less. More preferably, the predetermined length may be 0.8 mm or less. More preferably, the predetermined length may be 0.5 mm or less.

As described above, the second sealing member 2300 may have a shape having the first external diameter D5 before the cartridge and the main body are completely fastened. On the other hand, when the cartridge and the main body are completely fastened, the perforating member 2130 of the filter module 2000 may perforate the cap of the cartridge. At this time, the second sealing member 2300 may receive pressure as described later in FIG. 15, and the second sealing member 2300 may be transformed into a shape having a second external diameter D6 corresponding to the width R1 of the inlet of the cartridge housing and inserted into the cartridge housing. In this case, the second external diameter D6 may be smaller than the first external diameter D5. Additionally, the second sealing member 2300 inserted into the inside of the cartridge housing may come in contact with or press the cap accommodated within the housing. Through this, the second sealing member 2300 may seal the inlet of the housing relatively strongly, and the amount of coolant emitted from the cartridge to the outside through the external surface of the perforating member 2130 may be minimized. Meanwhile, the cap accommodated within the housing may be pushed or transformed into the housing by being pressed with the second sealing member 2300.

The size and shape of the second sealing member 2300 may be appropriately selected or transformed depending on the shape and size defined by the inlet of the housing of the cartridge. Meanwhile, the first external diameter D5 may be greater than the width R1 of the inlet of the cartridge housing, and specifically, the first external diameter D5 may be greater than the width R1 of the inlet of the cartridge housing by 0-20%, 0-10%, or 0-5%. As described later, the second sealing member 2300 may be transformed when the main body and the cartridge are fastened and may be contracted and inserted into the inlet of the cartridge housing. Furthermore, the second sealing member 2300, which is inserted into the inside of the cartridge housing through the inlet of the cartridge housing, may be contracted in a third direction and at the same time expanded in the fourth direction by the pressure applied in the third direction of FIG. 15, so that a sealing surface may be further configured on the internal surface of the inlet of the cartridge housing and the sealing of the inlet of the cartridge housing is strengthened.

Figure 15:
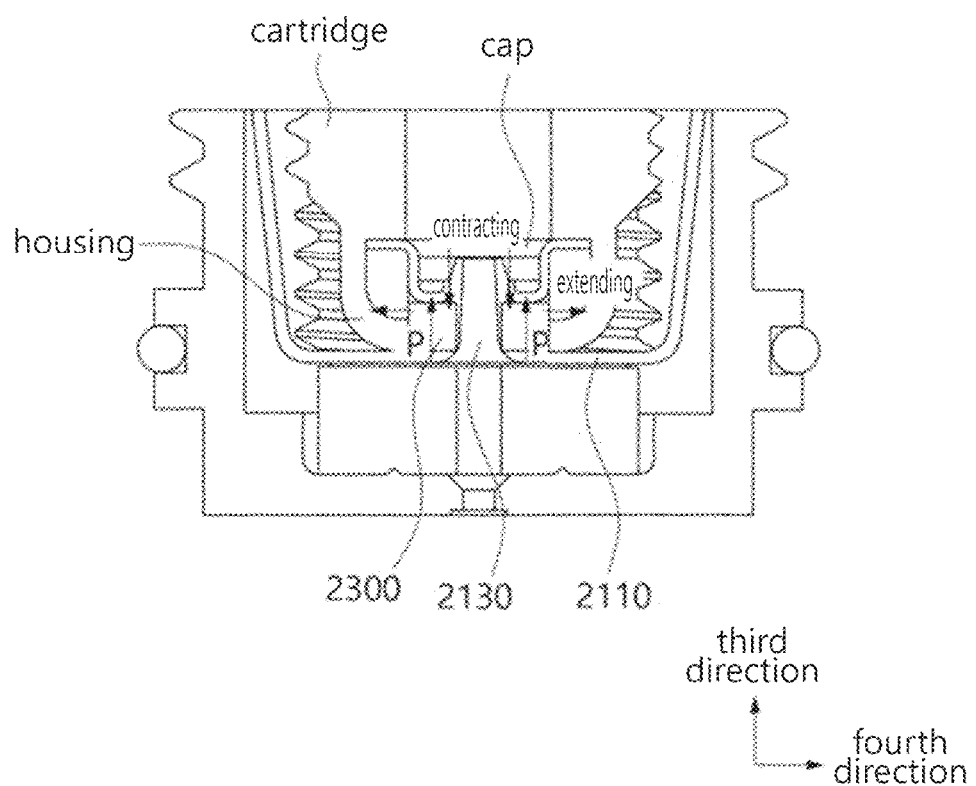
FIG. 15 is a view for explaining a principle that an external diameter of a second sealing member changes as a cartridge and a main body are fastened according to the second exemplary embodiment.

Refer to FIG. 15. FIG. 15 is a view for explaining a principle that the external diameter of the second sealing member changes as the cartridge and the main body are fastened according to the second exemplary embodiment.

When the coupling member of the cartridge and the connecting member of the main body are completely fastened, the filter module 2000 may be disposed between the cartridge and the main body. Additionally, when the filter module 2000 is disposed between the cartridge and the main body, the thickness of the second sealing member 2300 may be greater than the separation distance between the support surface 2110 and one end of the cartridge. Accordingly, when the second sealing member 2300 is subjected to pressure P by the support surface 2110 in the third direction perpendicular to the support surface 2110, at least a part of the second sealing member 2300 may be inserted into the inlet of the cartridge housing. For example, a part of the first external diameter D5 of the second sealing member 2300 that does not correspond to the width R1 of the inlet of the cartridge housing may be cut by the cartridge housing and may not be inserted into the cartridge housing when the main body and the cartridge are fastened, and the rest part may be inserted into the inside of the cartridge housing. In addition, after the second sealing member 2300 is inserted into the inside of the cartridge housing, the second sealing member 2300 may be transformed into a shape having the external diameter D6 corresponding to the width R1 defined by the inlet of the housing. Furthermore, the thickness of the second sealing member 2300 which is inserted into the inlet of the cartridge housing and disposed between the inlet of the cartridge housing and the cap is reduced in the third direction and is expanded in the fourth direction perpendicular to the third direction by pressure applied in the third direction. As a result, the second sealing member can additionally form a sealing surface not only in the third direction but also in the fourth direction and the cartridge housing.

In other words, the second sealing member 2300 may expand in the fourth direction and then seal the internal surface of the cartridge housing.

In this case, the second sealing member 2300 may be made of a material having a positive Poisson ratio, and may be made of a material having a yield stress of 50 MPa or less, more specifically 30 MPa or less, more specifically 20 MPa or less, and more specifically 5 MPa to 20 MPa.

Meanwhile, when the coupling member of the cartridge and the connecting member of the main body are completely fastened, the perforating member 2130 of the filter module 2000 may be inserted into the inside of the cartridge housing and then perforate the cap. Specifically, as described above, since the length of the perforating member 2130 is greater than the thickness (or height) of the second sealing member 2300, the perforating member 2130 may protrude to the outside and perforate the cap. Accordingly, the coolant stored in the cartridge may flow into the filter module 2000 through the perforating member 2130. At this time, the amount of the coolant leaking from the cartridge to the outside through the external surface of the perforating member 2130 may be significantly reduced because the second sealing member 2300 may relatively tightly seal the inlet of the housing of the cartridge.

Hereinafter, with referring to FIG. 16, experiments will be described in detail below in order to prove the effectiveness of preventing leakage of the coolant of the filter module 2000 including the second sealing member 2300 according to the present exemplary embodiment.

COMPARISON EXPERIMENT OF THE COOLANT LEAKAGE

Experimental Example

As an experimental example, prepared was a cartridge equipped with the filter module 2000 in which the filter 2400 having multiple feet and the second sealing member 2300 according to an exemplary embodiment of the present disclosure are disposed within the filter accommodation member 2100. Specifically, used was the filter module 2000 in which the filter with five feet, the first sealing member 2200 having an external diameter of about 9.3 mm, and the second sealing member 2300 having an external diameter of about 5.6 mm were disposed within the filter accommodation member 2100. For the experimental group, a coolant leakage experiment was conducted using a cartridge containing 74 g of a coolant.

Comparative Example

As a comparative example, prepared was a cartridge equipped with the filter module 2000 in which a circular filter, the first sealing member with an external diameter of about 9.3 mm, and the second sealing member with an external diameter of about 9.3 mm were disposed within the filter accommodation member 2100. Specifically, used was a circular filter which has substantially the same area as the area defined by the accommodation surface 2120 of the filter accommodation member 2100, and the second sealing member sealed the cartridge by making a contact surface with the inlet of the housing of the cartridge without being inserted into the inside of the cartridge housing even when the cartridge and the main body was fastened. For the comparison group, a coolant leakage experiment was also conducted using a cartridge containing 74 g of coolant.

Experimental Method

The weight of the cartridge over time was measured by applying the same fastening force to the cartridge equipped with the filter module which was prepared according to the comparative example and the experimental example. Additionally, the coolant consumption of the cartridge, that is, the coolant leakage amount, was measured based on the initial cartridge weight and the weight of the cartridge over time.

Experiment Results

FIG. 16 is a table showing the results of the coolant leakage experiments. Referring to FIG. 16, in the case of the comparison group, the weight of the cartridge was initially measured to be 74 g, but the weight of the cartridge was measured to be 0 g after 8 hours. In other words, it was confirmed that the coolant stored in the cartridge was completely consumed in the comparison group after 8 hours.

On the other hand, in the case of the experimental group, the weight of the cartridge was initially measured to be 74 g, and the weight of the cartridge was measured to be 68.7 g even after 72 hours for only one experiment, and in the other experiments, the weight of the cartridge was measured to be 74 g. In other words, in the case of the experimental example, it was confirmed that the coolant stored in the cartridge hardly leaked even after 72 hours had elapsed.

Through the results of this experiment, it could be proven that the effectiveness of preventing the coolant leakage is considerably improved when using the second sealing member 2300 according to an exemplary embodiment of the present disclosure.

Experimental Analysis

In the case of the comparative example, the sealing member is not inserted into the inside of the cartridge housing, but seals the coolant by making surface contact with the external surface of the housing. Meanwhile, the sealing pressure, which may indicate sealing performance, is defined as the force applied to the contact surface per unit contact cross-sectional area. At this time, in the case of sealing by a surface contact, the sealing pressure varies depending on the contact cross-sectional area. In particular, as the contact cross-sectional area increases, the sealing pressure decreases, so the sealing performance decreases and the possibility of the coolant leakage may increase. Additionally, in the case of the surface contact, there is a disadvantage in that the sealing performance becomes irregular depending on the type of a cartridge or the surface condition of a cartridge. Due to these factors, in the case of the comparative example, it is expected that the leakage of the coolant progressed within a short period of time.

On the other hand, in the case of the experimental example, the second sealing member is transformed into a form that blocks the entire inlet of the cartridge housing. Therefore, the possibility of coolant leaking is significantly reduced. In addition, when sealing members are inserted into the inside of the housing to perform sealing as in the experimental example, there is an advantage in that a high sealing effect may be provided regardless of the surface of the cartridge and the internal surface of the housing. Through this, it is expected that the coolant hardly leaked in the case of the experimental example.

Additionally, in the case of the experimental example, it was possible to prevent leakage of the coolant flowing from the cap of the cartridge into the perforating member even with a relatively weak fastening force. Specifically, in the case of the comparative example where the sealing member performed a sealing function through the surface contact with the "external surface" of the cartridge housing, a relatively strong fastening force, such as a force of 2500 N*m or more, specifically, a fastening force in the range of 2500 N*m to 3500 N*m, did not prevent leakage of the coolant emitted from the cartridge to the outside. In addition, when a strong fastening force in the range of 2500 N*m to 3500 N*m is applied to the cooling device, it may greatly affect the durability of the cooling device in terms of applying a strong force to the cooling device. For example, when a strong fastening force in the range of 2500 N*m to 3500 N*m is applied to the cooling device, damage may occur to the cooling device or components in the cooling device.

On the other hand, the second sealing member 2300 according to the second exemplary embodiment of the present disclosure may prevent leakage of the coolant from the cartridge to the perforating member even with a relatively weak fastening force, for example, a force of 2500 N*m or less, specifically, a fastening force in the range of 1600 N*m to 2500 N*m. This is presumably because the second sealing member 2300 is inserted within the cartridge housing and seals the internal surface of the inlet of the cartridge housing. In other words, according to the experimental example, provided is an advantageous effect of achieving a sealing effect of preventing leakage of the coolant while maintaining the durability of the cooling device in that a relatively weak fastening force is applied to the cooling device and the coolant leaking to the outside from the cartridge may be minimized.

In FIGS. 12 to 16, the description mainly focused on the second sealing member having a size and shape that may be transformed to an external diameter inserted into an inlet of a cartridge housing. However, the size or shape of the second sealing member shown in FIGS. 12 to 16 are only examples for the convenience of explanation, and the shape or size of the second sealing member can be appropriately changed to prevent leakage of the coolant emitted from the coolant storage unit. For example, the second sealing member may be provided with a shape having an external diameter corresponding to a width of the shape defined by the inlet of the cartridge housing while enclosing an external surface of the perforating member so that second sealing member may be inserted into the cartridge housing without transformation and seal the inlet of the housing when the perforating member may perforate the cap.

Hereinafter, referring to FIGS. 17 and 18, the coupling relationship between a filter module 3000 and a coolant storage unit will be described in detail when using the filter module 3000 according to a third exemplary embodiment described above. In this case, the cartridge type is mainly described as the coolant storage unit, but this is only for the convenience of description, and the technical idea of the present disclosure is not limited thereto. For example, the coupling relationship between the filter module 3000 and the cartridge to be described later may be equally applied even when the filter module 3000 is coupled with the coolant transfer unit (e.g. hose) of the coolant storage unit.

Figure 17:
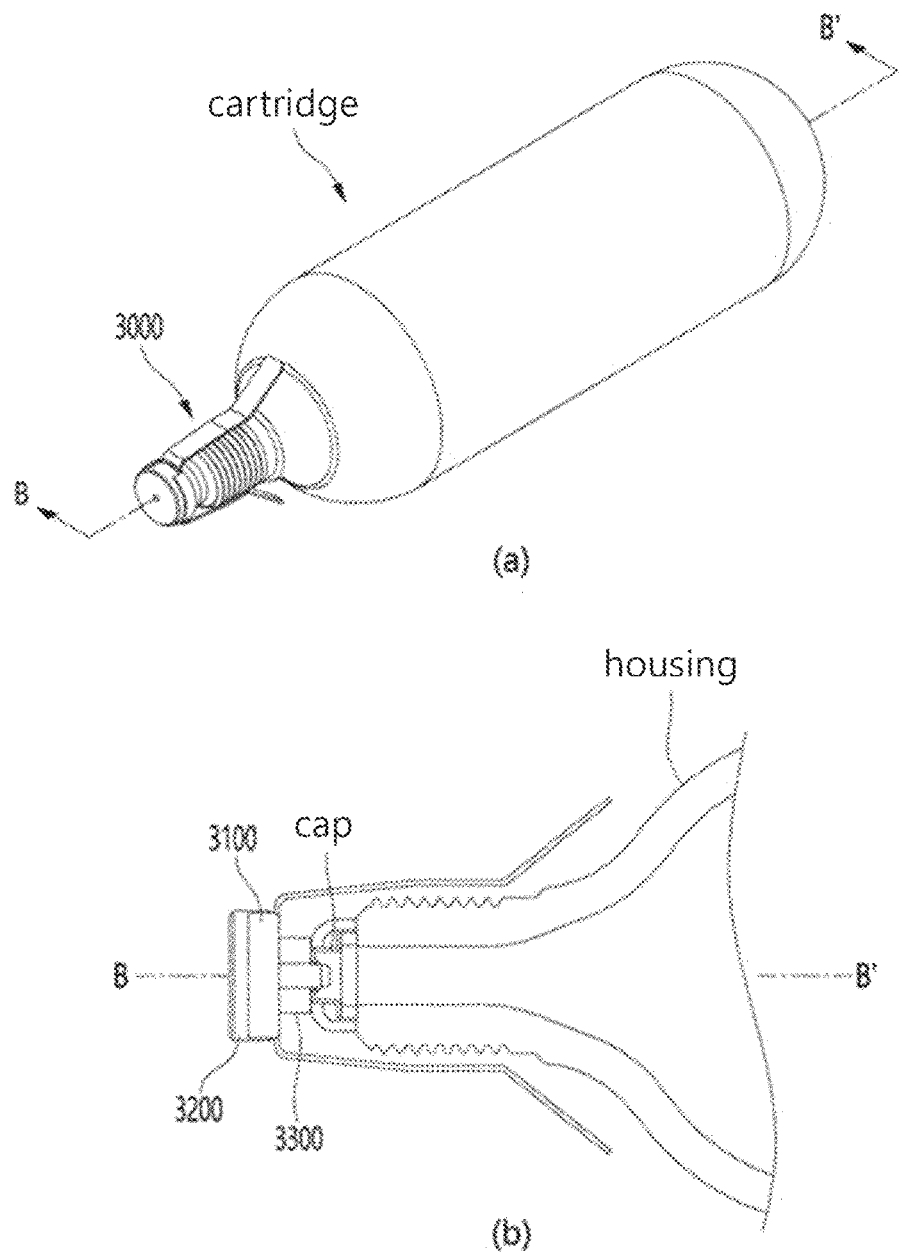
FIG. 17 is a view showing a cross-section of a filter module and a cartridge according to a third exemplary embodiment after the cartridge of the present disclosure and a main body are fastened.

FIG. 17 is a cross-sectional view showing a filter module 3000 and a cartridge according to the third exemplary embodiment after the cartridge and a main body of the present disclosure are fastened. In FIG. 17, the main body is not shown for the convenience of explanation, but it may be understood that the cartridge is coupled to the main body as shown in FIG. 14 or FIG. 15.

Referring to FIG. 17, the filter module 3000 according to the third exemplary embodiment of the present disclosure may include a filter accommodation member 3100, a first sealing member 3200, a second sealing member 3300, and a filter. Here, the filter accommodation member 3100 may be implemented similarly to the filter accommodation member 1100 of the filter module 1000 according to the first exemplary embodiment described above or the filter accommodation member 2100 of the filter module 2000 according to the second exemplary embodiment. In addition, the first sealing member 3200 may be implemented similarly to the first sealing member 1200 of the filter module 1000 according to the first exemplary embodiment described above or the first sealing member 2200 of the filter module 2000 according to the second exemplary embodiment. In addition, the content of the filter 1400 of the filter module 1000 according to the first exemplary embodiment described above or the contents of the filter 2400 of the filter module 2000 according to the second exemplary embodiment may be applied equally to the filter according to the third exemplary embodiment.

The second sealing member 3300 of the filter module 3000 according to the third exemplary embodiment may be implemented similarly to the second sealing member 1300 of the filter module 1000 according to the first exemplary embodiment or the second sealing member 2300 of the filter module 2000 according to the second exemplary embodiment within a range that does not conflict with the following description.

Figure 18:
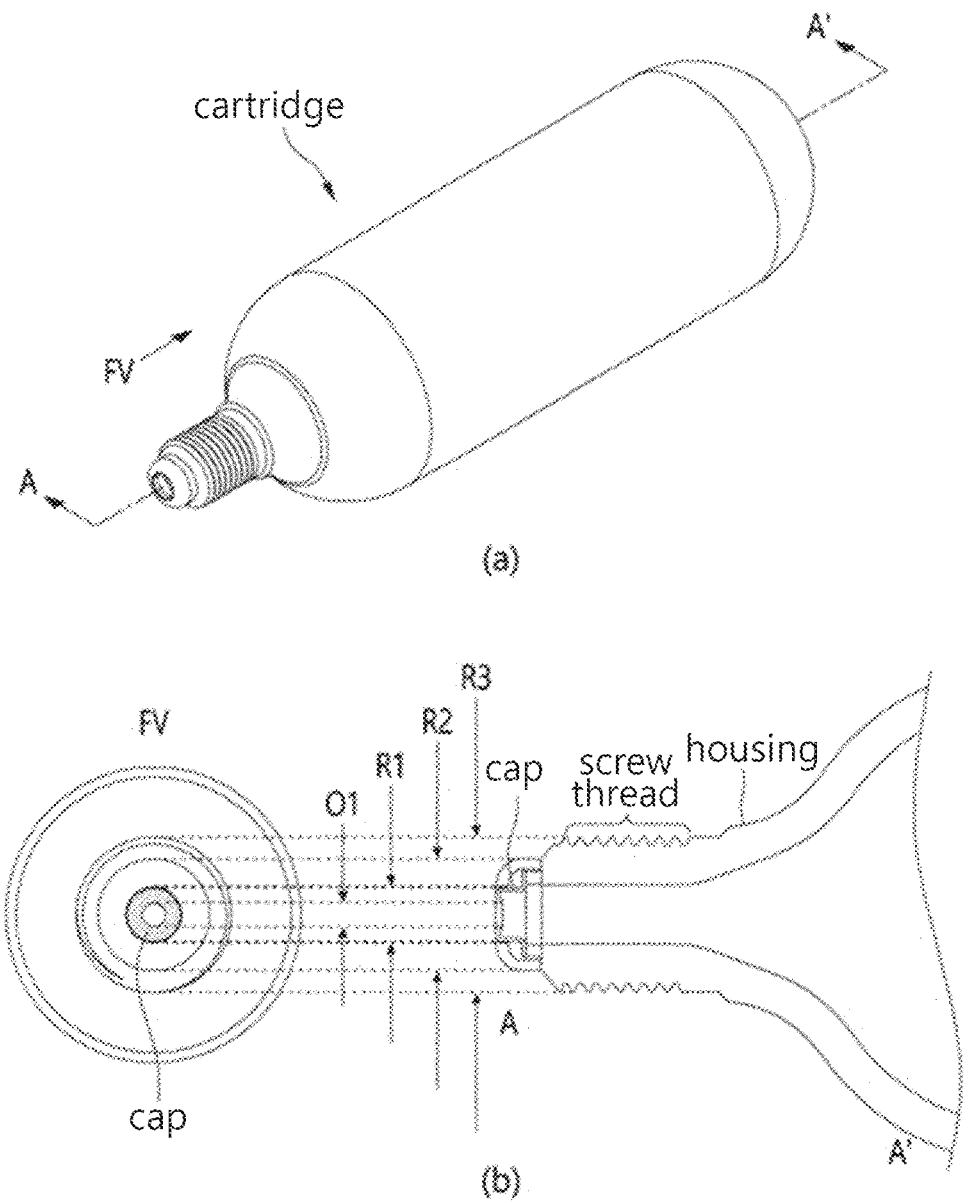
FIG. 18 is a view showing a structure of a cartridge according to an exemplary embodiment of the present disclosure.

Referring to FIG. 18, a structure of a cartridge will be described in more detail before describing the second sealing member 2300 according to the third exemplary embodiment in detail.

FIG. 18 is a view showing a structure of a cartridge according to an exemplary embodiment of the present disclosure.

Referring to FIG. 18, the cartridge may include a housing for storing the coolant, a coupling member formed on the external surface of the housing, a pressure unit, and a cap inserted into the inside of the housing.

Since the contents described in other parts of the present disclosure are applied to the housing, the coupling member, and the cap, overlapping parts may be omitted.

The pressure unit may refer to a part that presses the filter module 3000 in the process of coupling the cartridge to the main body through the filter module 3000. As the pressure unit is sufficiently in close contact with the filter module 3000 according to the coupling of the cartridge and the main body, leakage of the coolant may be prevented while the cooling device is operating. The pressure unit may include the housing inlet described above.

Referring to (b) of FIG. 18, each component of the cartridge may have an arbitrary width when the cartridge is viewed from the front (FV). Specifically, the width R1 of the housing inlet, the width R2 of the pressure unit, and the width R3 of the part of the coupling member may be sequentially defined based on the width O1 of the through-hole of the narrowest cap.

Referring again to FIG. 17, when the cartridge press the filter module 3000 as the cartridge and the main body are fastened, the pressure unit of the cartridge may press the second sealing member 3300 of the filter module 3000.

However, unlike the second exemplary embodiment, the second sealing member 3300 of the filter module 3000 is not inserted into the housing of the cartridge. In other words, the perforating member of the filter module 3000 may perforate the cap of the cartridge even in a state when the pressure unit of the housing presses against the second sealing member 3300 of the filter module 3000.

Leakage of the coolant may be prevented as the pressure unit of the cartridge and the second sealing member 3300 of the filter module 3000 come into close contact with each other.

At this time, the second sealing member 3300 may be set in consideration of the size of each component of the cartridge. For example, the external diameter of the second sealing member 3300 may be larger than the width O1 of the through-hole of the cap. Alternatively, the external diameter of the second sealing member 3300 may be larger than the width O1 of the through-hole of the cap and smaller than the width R1 of the housing inlet. Alternatively, the external diameter of the second sealing member 3300 may be larger than the width R1 of the housing inlet and smaller than the width R2 of the pressure unit. Alternatively, the external diameter of the second sealing member 3300 may be larger than the width R2 of the pressure unit and smaller than the width R3 of part of the coupling member. In the third exemplary embodiment, the external diameter of the second sealing member 3300 is preferably larger than the width R1 of the housing inlet and smaller than the width R2 of the pressure unit in order to prevent leakage of the coolant and facilitate manufacturing.

While the above description has focused on the case where the coolant storage unit is a cartridge, the technical ideas herein are not limited thereto and may be similarly applied to cases where the coolant storage unit includes a tank for storing the coolant and the coolant transfer unit (e.g., a hose) for transferring the coolant and the coolant transfer unit is connected to the second sealing member 3300 of the filter module 3000.

Hereinafter, a secondary filter module will be described with reference to FIG. 19.

The main purpose of the filter modules 1000, 2000, and 3000 of a variety of exemplary embodiments described above is to prevent impurities included in the coolant from flowing into the main body in the process when the coolant storage unit is coupled to the main body. Meanwhile, it is necessary to prevent foreign substances from entering the main body even when the coolant storage unit is not coupled to the main body, and for this purpose, an additional secondary filter module may be required in addition to the filter modules 1000, 2000, and 3000 described above.

Hereinafter, a case in which the filter module 1000 according to the first exemplary embodiment is used in the cooling device is mainly described for the convenience of description, but the technical idea of the present disclosure is not limited thereto, and the description of the secondary filter module described later may be not only applied to a case in which the filter module 2000, 3000 according to the second exemplary embodiment or the third exemplary embodiment is used but also equally applied to a case in which another type of filter module is used or a case in which the filter module is not used.

Figure 19:
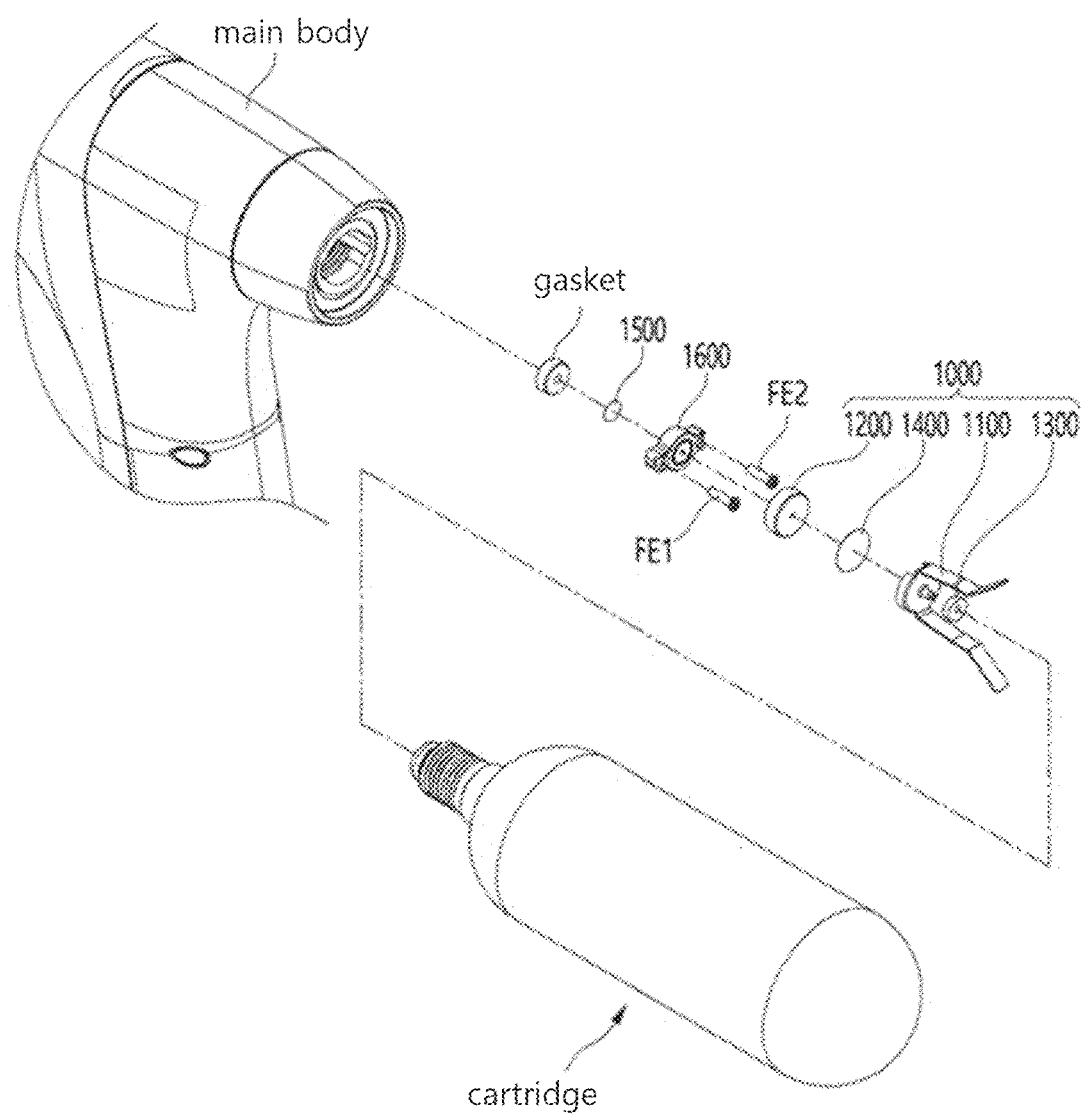
FIG. 19 is a view showing a second filter module according to an exemplary embodiment of the present disclosure.

FIG. 19 is a view showing the secondary filter module according to an exemplary embodiment of the present disclosure. Hereinafter, for the convenience of description, the existing filter module 1000 will be referred to as the first filter module and the filter 1400 will be referred to as the first filter.

Referring to FIG. 19, the second filter module may include the second filter 1500 and the second filter accommodation member 1600.

The second filter 1500 may be manufactured from a variety of materials. For example, the second filter 1500 may be manufactured from a variety of materials such as paper, metal, synthetic fiber, or polymer compounds.

The second filter 1500 may be reused several times when using the cooling device, and in this case, the material of the second filter 1500 may include a metal material such as stainless steel or nickel. When the material of the second filter 1500 is metal, durability is secured compared to a case where the material is paper, and thus it may be reusable. However, the second filter 1500 may be a one-time filter that has to be replaced whenever the cooling device is used, and in this case, the second filter 1500 may be implemented as a paper filter to reduce the manufacturing costs.

The second filter 1500 and the first filter 1400 may be manufactured from different materials. For example, the first filter 1400 may be a consumable filter made of paper, and the second filter 1500 may be a recyclable filter made of metal.

The second filter 1500 may be implemented in the form of a mesh net. For example, the second filter 1500 may be in the form of a net including a plurality of pores with a predetermined size.

The second filter 1500 may be implemented in a variety of shapes. For example, the second filter 1500 may be implemented in a disk shape with a predetermined diameter and a circular cross-section or a disk shape with a predetermined width and a square cross-section.

The second filter 1500 may have a similar shape to the first filter 1400. However, the size of the first filter 1400 may be larger than or equal to the size of the second filter 1500. Alternatively, the second filter 1500 may have a different shape from the first filter 1400. For example, the second filter 1500 may be in a disk shape with a circular cross-section, and the first filter 1000 may be in a disk shape with a polygonal cross-section including at least one protrusion.

The second filter accommodation member 1600 may accommodate the second filter 1500. The second filter accommodation member 1600 may include an inner space for accommodating the second filter 1500.

The second filter accommodation member 1600 may be coupled to the main body. For example, referring to FIG. 19, the second filter accommodation member 1600 may be fixed to the main body through fixing members FE1 and FE2. In the process of coupling the second filter accommodation member 1600 to the main body, a gasket may be accommodated in the inner space of the second filter accommodation member 1600.

The gasket is embedded in the main body of the cooling device, and is fluidly connected to the valve to guide the flow of the coolant. Specifically, the gasket is connected to the valve or a conduit connected to the valve, and when the coolant storage unit is coupled to the main body, it is fluidly connected to the coolant storage unit so that the coolant in the coolant storage unit may move to the valve through the gasket.

The gasket may have a variety of shapes. The gasket, for example, may be implemented in the form of a disk with a circular cross-section. As another example, the gasket may be implemented in a disk shape having a cross-section corresponding to the shape of the second filter 1500.

The gasket may support the second filter 1500. For example, the second filter 1500 may be disposed in a state of the surface contact with the gasket. At this time, the shape of the gasket may correspond to the shape of the second filter 1500. In this case, the gasket may be understood as the second filter support unit.

The gasket may include pores for the coolant to move through. As the second filter 1500 is positioned on one side of the gasket, one end of the pore of the gasket may be partially obscured by the second filter 1500. In other words, the second filter 1500 may prevent foreign substances from flowing into one end of the pore of the gasket.

As the second filter accommodation member 1600 is coupled to the main body and the gasket is accommodated in the inner space of the second filter accommodation member 1600, the second filter 1500 may be disposed between the gasket and the second filter accommodation member 1600.

When the second filter module is coupled with the main body as described above, the second filter 1500 may be disposed between the part where the coolant moves in the cooling device (e.g. a conduit through which the coolant flows) and the outside, thereby preventing foreign substances from entering the cooling device in a state of not using the cooling device.

In addition, in the process of coolant flowing from the coolant storage unit (e.g., cartridge) into the cooling device, the coolant may move to the gasket through at least the second filter accommodation member 1600 and the second filter 1500, and impurities may be filtered in the process. Furthermore, the first filter module 1000 is disposed of between the second filter module and the coolant storage unit so that impurities contained in the coolant may be filtered several times in the process in which the coolant flows into the cooling device.

The features, structures, effects or the like described above in the exemplary embodiments are included in at least one exemplary embodiment of the present disclosure and are not necessarily limited to one exemplary embodiment. Furthermore, the features, structures, effects, or the like exemplified in each exemplary embodiment may be combined or modified in other exemplary embodiments by a person having ordinary knowledge in the field to which the exemplary embodiments belong. Therefore, the contents related to such combinations and modifications should be interpreted as being included in the scope of the present disclosure.

In addition, although the exemplary embodiments have been described above, it is only an example and does not limit the present disclosure, and one having ordinary knowledge in the field to which the present disclosure belongs will realize that a variety of modifications and applications not shown above are possible without deviating from the essential characteristics of the exemplary embodiments. In other words, each component specifically shown in the exemplary embodiments may be implemented by modifying it. Differences in such variations and applications are to be construed as falling within the scope of the present disclosure as defined by the appended claims.

What is claimed is:

1. A filter module accommodating a filter for filtering out impurities from a coolant emitted from a cartridge comprising a housing and a cap, the filter module comprising:
a filter accommodation member comprising:
a support surface having a plate shape,
an accommodation surface located on an edge of the support surface and protruding in a first direction from a first side of the support surface, and a perforating member located at a center of the support surface and protruding in a second direction from a second side of the support surface; and a second sealing member having a first external diameter and comprising a through-hole having a width greater than a width of the perforating member so that the perforating member is fitted into the through-hole of the second sealing member, wherein, in response to the cap being connected by the perforating member, the second sealing member is configured to be transformed into a shape having a second external diameter corresponding to a width of an inlet of the housing accommodating the cap, and inserted into an inside of the housing to press the cap, and wherein the second external diameter is smaller than the first external diameter.

2. The filter module of claim 1, wherein the second sealing member has a shape corresponding to a shape of the inlet of the housing.

3. The filter module of claim 1, wherein a length of the perforating member is greater than a height of the second sealing member so that in response to the perforating member being fitted into the through-hole of the second sealing member, the perforating member is configured to protrude to an outside of the second sealing member.

4. The filter module of claim 1, wherein the filter module further comprises a first sealing member disposed at an inner side of the accommodation surface and having a third external diameter smaller than a width of the accommodation surface, and wherein the filter is disposed between the first sealing member and the filter accommodation member.

5. The filter module of claim 4, wherein the first external diameter of the second sealing member is smaller than the third external diameter of the first sealing member.

6. The filter module of claim 4, wherein the first sealing member comprises Teflon or Nylon 6-6, and wherein the second sealing member comprises Teflon or Nylon 6-6.

7. A cooling device for spraying a coolant, the cooling device comprising:

a cartridge comprising:

a cap configured to prevent external leakage of the coolant, and a housing configured to accommodate the cap therein and comprising a coupling member formed on an external surface of the housing and configured to store the coolant;

a main body accommodating a nozzle configured to spray the coolant and a valve configured to control a flow of the coolant, the main body comprising a connecting member fastened to the coupling member of the housing of the cartridge; and a filter module comprising:

a filter accommodation member comprising:

a support surface having a plate shape, an accommodation surface located on an edge of the support surface and protruding in a first direction from a first side of the support surface, a perforating member located at a center of the support surface, protruding in a second direction from a second side of the support surface and perforating the cap, and a second sealing member having a first external diameter and comprising a through-hole having a width greater than a width of the perforating member, the perforating member configured to be fitted into the through-hole of the second sealing member, wherein, in response to the cap being connected by the perforating member, the second sealing member is configured to be transformed into a shape having a second external diameter corresponding to a width of an inlet of the housing accommodating the cap, and inserted into an inside of the housing to press the cap, and wherein the second external diameter is smaller than the first external diameter.

8. The cooling device of claim 7, wherein the filter module is disposed between the cartridge and the main body, wherein the second sealing member is configured to be changed to a shape having the second external diameter by receiving pressure in a third direction perpendicular to the support surface and inserted into the inlet of the housing in response to the connecting member and the coupling member being fastened, and wherein the second sealing member disposed at the inlet of the housing is configured to receive pressure in the third direction and extend in a fourth direction perpendicular to the third direction to seal the housing.

9. The cooling device of claim 7, wherein the second sealing member has a shape corresponding to a shape of the inlet of the housing.

10. The cooling device of claim 7, wherein a length of the perforating member is greater than a height of the second sealing member so that in response to the second sealing member being fitted into the perforating member, the perforating member is configured to protrude to an outside of the second sealing member.

11. The cooling device of claim 7, the filter module further comprising:

a first sealing member disposed at an inner side of the accommodation surface and having a third external diameter smaller than a width of the accommodation surface; and a filter disposed between the first sealing member and the filter accommodation member.

12. The cooling device of claim 11, wherein the first external diameter of the second sealing member is smaller than the third external diameter of the first sealing member.

13. The cooling device of claim 11, wherein the first sealing member comprises Teflon or Nylon 6-6, and wherein the second sealing member comprises Teflon or Nylon 6-6.

* * * * *